(12) United States Patent
Kordyum et al.

(10) Patent No.: US 6,773,899 B2
(45) Date of Patent: Aug. 10, 2004

(54) PHAGE-DEPENDENT SUPERPRODUCTION OF BIOLOGICALLY ACTIVE PROTEIN AND PEPTIDES

(75) Inventors: Vitaliy A. Kordyum, Kiev (UA); Iryna Yu. Slavchenko, Kiev (UA); Svitlana I. Chernykh, Kiev (UA); Oleksandr F. Vozianov, Kiev (UA)

(73) Assignee: Phage Biotechnology Corporation, Tustin, CA (US)

( * ) Notice: Subject to any disclaimer, the term of this patent is extended or adjusted under 35 U.S.C. 154(b) by 0 days.

(21) Appl. No.: 09/929,918

(22) Filed: Aug. 15, 2001

(65) Prior Publication Data

US 2002/0090678 A1 Jul. 11, 2002

Related U.S. Application Data

(60) Provisional application No. 60/225,437, filed on Aug. 15, 2000.

(51) Int. Cl.[7] .......................... C12P 21/00; C12P 21/02; C12N 15/70
(52) U.S. Cl. .................. 435/69.1; 435/69.4; 435/69.51
(58) Field of Search .............................. 435/69.1, 69.4, 435/69.51

(56) References Cited

U.S. PATENT DOCUMENTS

| | | | |
|---|---|---|---|
| 4,637,980 A | * | 1/1987 | Auerbach et al. .......... 435/69.3 |
| 5,395,756 A | | 3/1995 | Igarashi |
| 5,401,721 A | | 3/1995 | Folkman et al. |

FOREIGN PATENT DOCUMENTS

| | | | |
|---|---|---|---|
| GB | 2 143 238 A | 2/1985 | |
| GB | 2143238 A | * 2/1985 | ............ A12N/9/00 |

OTHER PUBLICATIONS

Miao et al. Biotechnol. Prog. 9:153–159, 1993.*
Chen et al (Journal of Biotechnology 40:87097, 1995).*
Lin et at (Biotechnology and Bioengineering 57:529–35, 1998).*

* cited by examiner

Primary Examiner—Mary E. Mosher
(74) Attorney, Agent, or Firm—Knobbe, Martens, Olson & Bear, LLP

(57) ABSTRACT

This invention relates to a method for enhancing the production of biologically active proteins and peptides in bacterial cells by infecting bacterial cells of the producer strain, which contain a plasmid with one or more targeted genes, with bacteriophage λ with or without the targeted gene(s). The targeted genes encoding the biologically active proteins are under the control of a T7 polymerase promoter and the bacteria also are capable of expressing the gene for T7 RNA polymerase. The phage increases synthesis of the targeted protein and induces lysis of the producer strain cells. Superproduction is achieved by the combination of the high level of expression achieved from the T7 polymerase promoter and by cultivating the producer strain cells under culture conditions that delay lytic development of the phage. The biologically active proteins and peptides subsequently accumulate in a soluble form in the culture medium as the cells of the producer strain are lysed by the phage.

23 Claims, 12 Drawing Sheets

```
                    BsaBI
                    ---------
           BsaBI
           ---------
      BglII         VspI         BfmI         MbiI          XbaI
      ------        ------       ------       ------        ------
4951 GCGTAGAGGATCGAGATCTCGATCCCGCGAAATTAATACGACTCA CTATAGGGGAATTGTGAGCGGATAACAATTCCCCTCTAGAAATAA
     CGCATCTCCTAGCTCTAGAGCTAGGGCGCTTTAATTATGCTGAGT GATATCCCCTTAACACTCGCCTATTGTTAAGGGGAGATCTTTATT
```

```
  +2                               MetAlaGluGlyGlu IleThrThrPheThrAlaLeuThrGluLysPheAsnLeuProPr
                                                   HpaI
                                                   ------
                                         HindII                         SmaI
                                         ------                         --
                          NdeI  Eco57I   HincII                         AvaI
                          ------ ------  ------                         --
5041 TTTTGTTTAACTTTAAGAAGGAGATATACATATGGCTGAAGGGGA AATCACCACCTTTACAGCGTTAACGGAGAAATTTAACCTTCCGCC
     AAAACAAATTGAAATTCTTCCTCTATATGTATACCGACTTCCCCT TTAGTGGTGGAAATGTCGCAATTGCCTCTTTAAATTGGAAGGCGG
```

```
  +2 oGlyAsnTyrLysLysProLysLeuLeuTyrCysSerAsnGlyGly HisPheLeuArgIleLeuProAspGlyThrValAspGlyThrAr
     SmaI                       PstI
     ----                       ------

AvaI           HindIII     BfmI                   EcoRI                           NruI
     ----           ------      ------                 ------                          ---
5131 CGGGAATTACAAAAAACCCAAGCTTCTTTACTGCAGTAACGGAGG ACACTTCCTGCGAATTCTGCCAGATGGCACAGTAGATGGGACTCG
     GCCCTTAATGTTTTTTGGGTTCGAAGAAATGACGTCATTGCCTCC TGTGAAGGACGCTTAAGACGGTCTACCGTGTCATCTACCCTGAGC
```

```
  +2 gAspArgSerAspGlnHisIleGlnLeuGlnLeuSerAlaGluSer ValGlyGluValTyrIleLysSerThrGluThrGlyGlnTyrLe
                                                   SalI
                                                   ------
     PvuI                                                         HindII           RsaI
     ------                                                       ------           ----

NruI             PvuII        XmaIII                         HincII           MlsI Csp6I
     ---              ------       ------                         ------           ----------
5221 CGATCGCTCCGACCAGCACATTCAGCTGCAACTCTCGGCCGAAAG CGTTGGAGAGGTCTATATCAAGTCGACGGAGACTGGCCAGTACCT
     GCTAGCGAGGCTGGTCGTGTAAGTCGACGTTGAGAGCCGGCTTTC GCAACCTCTCCAGATATAGTTCAGCTGCCTCTGACCGGTCATGGA
```

```
  +2 uAlaMetAspThrAspGlyLeuLeuTyrGlySerGlnThrProAsn GluGluCysLeuPheLeuGluArgLeuGluGluAsnHisTyrAs
     StyI
     -----

NcoI                                          Mva1269I     XbaI
     ------                                        --------     ------
5311 TGCCATGGACACCGATGGGCTTCTGTATGGCTCACAGACGCCTAA CGAAGAATGCTTGTTTCTAGAAAGACTAGAAGAAAACCATTACAA
     ACGGTACCTGTGGCTACCCGAAGACATACCGAGTGTCTGCGGATT GCTTCTTACGAACAAAGATCTTTCTGATCTTCTTTTGGTAATGTT
```

```
  +2 nThrTyrIleSerLysLysHisAlaGluLysAsnTrpPheValGly LeuLysLysAsnGlySerCysLysArgGlyProArgThrHisTy
     RsaI
     ----

Csp6I                           StuI
     ------                          ------
5401 CACGTACATATCGAAAAAACATGCAGAGAAGAACTGGTTTGTAGG CCTTAAAAAAAATGGTTCCTGTAAGCGTGGACCACGGACTCACTA
     GTGCATGTATAGCTTTTTTGTACGTCTCTTCTTGACCAAACATCC GGAATTTTTTTTACCAAGGACATTCGCACCTGGTGCCTGAGTGAT
```

```
  +2 rGlyGlnLysAlaIleLeuPheLeuProLeuProValSerSerAsp ***
                                                     SalI              XmaIII
                                                     ------            ------
                              SacI               EcoRI SacI HindII     XhoI
                              -----              ------------ ------    -
      MlsI                    Ecl136II           BamHI Ecl136IIHincIIHindIII NotIAvaI
      -----                   -------            -----  -----------------------
5491 TGGCCAAAAGGCTATCTTGTTCCTGCCACTACCAGTGAGCTCCGA CTAAGGATCCGAATTCGAGCTCCGTCGACAAGCTTGCGGCCGCAC
     ACCGGTTTTCCGATAGAACAAGGACGGTGATGGTCACTCGAGGCT GATTCCTAGGCTTAAGCTCGAGGCAGCTGTTCGAACGCCGGCGTG
```

**CHEMICALLY SYNTHESIZED haFGF GENE AND
CORRESPONDING AMINO ACID SEQUENCE**

*FIG. 1*

| | | | | | | | | |
|---|---|---|---|---|---|---|---|---|
| FGF fr HUMECGFB | TTC | GCC | CTG | ACC | AAG | AAT CTG | CCT | CCA |
| haFGF 155 | TTT | GCG | TTA | ACG | AAA | AAC CTT | CCG | CCC |
| № amino acid | 009 | 011 | 012 | 013 | 015 | 017 018 | 019 | 020 |
| | Phe | Ala | Leu | Thr | Lys | Asn Leu | Pro | Pro |

| | | | | | | | | |
|---|---|---|---|---|---|---|---|---|
| FGF fr HUMECGFB | AAG | AAG | AAA | CTC | CTC | TGT | AGC | GGG | GGC |
| haFGF 155 | AAA | AAA | AAG | CTT | CTT | TGC | AGT | GGA | GGA |
| № amino acid | 024 | 025 | 027 | 028 | 029 | 031 | 032 | 034 | 035 |
| | Lys | Lys | Lys | Leu | Leu | Cys | Ser | Gly | Gly |

| | | | | | | | | |
|---|---|---|---|---|---|---|---|---|
| FGF fr HUMECGFB | AGG | ATC | CTT | CCG | GTG | ACA | AGG | GAC | AGG |
| haFGF 155 | CGA | ATT | CTG | CCA | GTA | ACT | CGC | GAT | CGC |
| № amino acid | 039 | 040 | 041 | 042 | 046 | 049 | 050 | 051 | 052 |
| | Arg | Ile | Leu | Pro | Val | Thr | Arg | Asp | Arg |

| | | | | | | | | |
|---|---|---|---|---|---|---|---|---|
| FGF fr HUMECGFB | AGC | CAG | AGT | GCG | GTG | GGG | GTG | ATA | AGT |
| haFGF 155 | TCC | CAA | TCG | GCC | GTT | GGA | GTC | ATC | TCG |
| № amino acid | 053 | 060 | 062 | 063 | 066 | 067 | 069 | 071 | 073 |
| | Ser | Gln | Ser | Ala | Val | Gly | Val | Ile | Ser |

| | | | | | | | | |
|---|---|---|---|---|---|---|---|---|
| FGF fr HUMECGFB | ACC | TTG | GAC | TTA | TAC | ACA | CCA | AAT | GAG |
| haFGF 155 | ACG | CTT | GAT | CTG | TAT | ACG | CCT | AAC | GAA |
| № amino acid | 074 | 080 | 085 | 088 | 089 | 093 | 094 | 095 | 096 |
| | Thr | Leu | Asp | Leu | Tyr | Thr | Pro | Asn | Glu |

| | | | | | | | | |
|---|---|---|---|---|---|---|---|---|
| FGF fr HUMECGFB | TGT | TTC | CTG | AGG | CTG | GAG | GAG | ACC | TAT |
| haFGF 155 | TGC | TTT | CTA | AGA | CTA | GAA | GAA | ACG | TAC |
| № amino acid | 098 | 100 | 101 | 103 | 104 | 105 | 106 | 111 | 112 |
| | Cys | Phe | Leu | Arg | Leu | Glu | Glu | Thr | Tyr |

| | | | | | | | | |
|---|---|---|---|---|---|---|---|---|
| FGF fr HUMECGFB | TCC | AAG | AAG | AAT | GTT | CTC | AAG | AAG | GGG |
| haFGF 155 | TCG | AAA | AAA | AAC | GTA | CTT | AAA | AAA | GGT |
| № amino acid | 114 | 115 | 116 | 121 | 124 | 126 | 127 | 128 | 130 |
| | Ser | Lys | Lys | Asn | Val | Leu | Lys | Lys | Gly |

| | | | | | | | | |
|---|---|---|---|---|---|---|---|---|
| FGF fr HUMECGFB | AGC | TGC | AAA | CGC | GGT | CCT | CAG | AAA | GCA |
| haFGF 155 | TCC | TGT | AAG | CGT | GGA | CCA | CAA | AAG | GCT |
| № amino acid | 131 | 132 | 133 | 134 | 135 | 136 | 142 | 143 | 144 |
| | Ser | Cys | Lys | Arg | Gly | Pro | Gln | Lys | Ala |

| | | | | | | | |
|---|---|---|---|---|---|---|---|
| FGF fr HUMECGFB | TTT | CTC | CCC | CTG | GTC | TCT | TCT | GAT |
| haFGF 155 | TTC | CTG | CCA | CTC | GTG | AGC | TCC | GAC |
| № amino acid | 147 | 148 | 149 | 150 | 152 | 153 | 154 | 155 |
| | Phe | Leu | Pro | Leu | Val | Ser | Ser | Asp |

MODIFICATION IN MOLECULE haFGF 155 CODONS.
FGF fr HUMECGFB-THE SEQUENCE FROM GENBANK(at NCBI), haFGF 155
—THE SEQUENCE SYNTHESIZED BY THE INVENTION AUTHORS.

*FIG.2*

HPLC PURIFIED FGF155(8-23-00)

LANE 1: 10 μl OF CONDITIONED MEDIUM
   2: 7 μl OF HEPARIN-SEPHAROSE PURIFIED(0.45 μg /μl)
   3: 14 μl OUT OF 80 μl OF HPLC-PURIFIED

```
                BsaBI
                ------
          BsaBI
          ------
       BglII            VspI            BfmI         MbiI              XbaI
       -----            ----            ----         ----              ----
4951 GCGTAGAGGATCGAGATCTCGATCCCGCGAAATTAATACGACTCA CTATAGGGGAATTGTGAGCGGATAACAATTCCCCTCTAGAAATAA
     CGCATCTCCTAGCTCTAGAGCTAGGGCGCTTTAATTATGCTGAGT GATATCCCCTTAACACTCGCCTATTGTTAAGGGGAGATCTTTATT

+2                         MetAsnTyrLysLys ProLysLeuLeuTyrCysSerAsnGlyGlyHisPheLeuArgIl
                                                             PstI
                                                             ----
                  NdeI                 HindIII   BfmI                                  EcoRI
                  ----                 -------   ----                                  -----
5041 TTTTGTTTAACTTTAAGAAGGAGATATACATATGAATTACAAAAA ACCCAAGCTTCTTTACTGCAGTAACGGAGGACACTTCCTGCGAAT
     AAAACAAATTGAAATTCTTCCTCTATATGTATACTTAATGTTTTT TGGGTTCGAAGAAATGACGTCATTGCCTCCTGTGAAGGACGCTTA +2 eLeuProAspGlyThrValAspGlyThrArgAspArgSerAspGln HisIleGlnLeuGlnLeuSerAlaGluSerValGlyGluValTy
                                       PvuI
                                       ----
        EcoRI                NruI                       PvuII        XmaIII
        -----                ----                       -----        ------
5131 TCTGCCAGATGGCACAGTAGATGGGACTCGCGATCGCTCCGACCA GCACATTCAGCTGCAACTCTCGGCCGAAAGCGTTGGAGAGGTCTA
     AGACGGTCTACCGTGTCATCTACCCTGAGCGCTAGCGAGGCTGGT CGTGTAAGTCGACGTTGAGAGCCGGCTTTCGCAACCTCTCCAGAT +2 rIleLysSerThrGluThrGlyGlnTyrLeuAlaMetAspThrAsp GlyLeuLeuTyrGlySerGlnThrProAsnGluGluCysLeuPh
            SalI
            ----
            HindII        RsaI       StyI
            ------        ----       ----
            HincII   MlsI Csp6I      NcoI                                           Mval269I
            ------   ---- -----      ----                                           --------
5221 TATCAAGTCGACGGAGACTGGCCAGTACCTTGCCATGGACACCGA TGGGCTTCTGTATGGCTCACAGACGCCTAACGAAGAATGCTTGTT
     ATAGTTCAGCTGCCTCTGACCGGTCATGGAACGGTACCTGTGGCT ACCCGAAGACATACCGAGTGTCTGCGGATTGCTTCTTACGAACAA +2 eLeuGluArgLeuGluGluAsnHisTyrAsnThrTyrIleSerLys LysHisAlaGluLysAsnTrpPheValGlyLeuLysLysAsnGl
                                       RsaI
                                       ----
        XbaI                   Csp6I                                   StuI
        ----                   -----                                   ----
5311 TCTAGAAAGACTAGAAGAAAACCATTACAACACGTACATATCGAA AAAACATGCAGAGAAGAACTGGTTTGTAGGCCTTAAAAAAAATGG
     AGATCTTTCTGATCTTCTTTTGGTAATGTTGTGCATGTATAGCTT TTTTGTACGTCTCTTCTTGACCAAACATCCGGAATTTTTTTACC +2 ySerCysLysArgGlyProArgThrHisTyrGlyGlnLysAlaIle LeuPheLeuProLeuProValSerSerAsp***
                                                                         SacI
                                                                         ----
                    MlsI                                      Ecl136II        BamHIEcoRI
                    ----                                      --------        ----------
5401 TTCCTGTAAGCGTGGACCACGGACTCACTATGGCCAAAAGGCTAT CTTGTTCCTGCCACTACCAGTGAGCTCCGACTAAGGATCCGAATT
     AAGGACATTCGCACCTGGTGCCTGAGTGATACCGGTTTTCCGATA GAACAAGGACGGTGATGGTCACTCGAGGCTGATTCCTAGGCTTAA SacI    SalI
     ----    ----
     EcoRI   HindII     XmaIII   XhoI
     -----   ------     ------   ----
     Ecl136IIHincIIHindIII NotI   AvaI
     -------------------- ----    ----
5491 CGAGCTCCGTCGACAAGCTTGCGGCCGCACTCGAGCACCACCACC ACCACCACTGAGATCCGGCTGCTAACAAAGCCCGAAAGGAAGCTG
     GCTCGAGGCAGCTGTTCGAACGCCGGCGTGAGCTCGTGGTGGTGG TGGTGGTGACTCTAGGCCGACGATTGTTTCGGGCTTTCCTTCGAC
```

NUCLEOTIDE AND AMINO ACID SEQUENCE FOR CHEMICALLY SYNTHESIZED HUMAN A FGF (134 AMINO ACIDS)

*FIG. 6*

```
                              BsaBI
                         - - - - - - - - - -
                   BsaBI
              - - - - - - - - - -
           BglII         VspI          BfmI          MboI          XbaI
           - - - - - -   - - - - - -   - - - - - -   - - - - - -   - - - - - -
4951  GCGTAGAGGATCGAGATCTCGATCCCGCGAAATTAATACGACTCA CTATAGGGGAATTGTGAGCGGATAACAATTCCCCTCTAGAAATAA
      CGCATCTCCTAGCTCTAGAGCTAGGGCGCTTTAATTATGCTGAGT GATATCCCCTTAACACTCGCCTATTGTTAAGGGGAGATCTTTATT
```

```
  +2                              MetPheAsnLeuPro ProGlyAsnTyrLysLysProLysLeuLeuTyrCysSerAsnGl
                                             SmaI                                      PstI
                                             - - - - - -                               - - - - - -
                          NdeI           AvaI               HindIII        BfmI
                          - - - - - -    - - - - - -        - - - - - -   - - - - - -
5041  TTTTGTTTAACTTTAAGAAGGAGATATACATATGTTTAACCTTCC GCCCGGGAATTACAAAAAACCCAAGCTTCTTTACTGCAGTAACGG
      AAAACAAATTGAAATTCTTCCTCTATATGTATACAAATTGGAAGG CGGGCCCTTAATGTTTTTTGGGTTCGAAGAAATGACGTCATTGCC
```

```
  +2 yGlyHisPheLeuArgIleLeuProAspGlyThrValAspGlyThr ArgAspArgSerAspGlnHisIleGlnLeuGlnLeuSerAlaGl
                                                                PvuI
                                                                - - - - - -
           EcoRI                         NruI                PvuII         XmaIII
           - - - - - -                   - - - - - -         - - - - - -   - - - - - -
5131  AGGACACTTCCTGCGAATTCTGCCAGATGGCACAGTAGATGGGAC TCGCGATCGCTCCGACCAGCACATTCAGCTGCAACTCTCGGCCGA
      TCCTGTGAAGGACGCTTAAGACGGTCTACCGTGTCATCTACCCTG AGCGCTAGCGAGGCTGGTCGTGTAAGTCGACGTTGAGAGCCGGCT
```

```
  +2 uSerValGlyGluValTyrIleLysSerThrGluThrGlyGlnTyr LeuAlaMetAspThrAspGlyLeuLeuTyrGlySerGlnThrPr
                 SalI
                 - - - - - -
                 HindII          RsaI          StyI
                 - - - - - -     - - - - -     - - - - - -
                 HincII          MlsI Csp6I    NcoI
                 - - - - - -     - - - - - - - - - - - - -
5221  AAGCGTTGGAGAGGTCTATATCAAGTCGACGGAGACTGGCCAGTA CCTTGCCATGGACACCGATGGGCTTCTGTATGGCTCACAGACGCC
      TTCGCAACCTCTCCAGATATAGTTCAGCTGCCTCTGACCGGTCAT GGAACGGTACCTGTGGCTACCCGAAGACATACCGAGTGTCTGCGG
```

```
  +2 oAsnGluGluCysLeuPheLeuGluArgLeuGluGluAsnHisTyr AsnThrTyrIleSerLysLysHisAlaGluLysAsnTrpPheVa
                                                             RsaI
                                                             - - - -
           Mval2691     XbaI                                 Csp6I
           - - - - - -  - - - - - -                          - - - -
5311  TAACGAAGAATGCTTGTTTCTAGAAAGACTAGAAGAAAACCATTA CAACACGTACATATCGAAAAAACATGCAGAGAAGAACTGGTTTGT
      ATTGCTTCTTACGAACAAAGATCTTTCTGATCTTCTTTTGGTAAT GTTGTGCATGTATAGCTTTTTTGTACGTCTCTTCTTGACCAAACA
```

```
  +2 lGlyLeuLysLysAsnGlySerCysLysArgGlyProArgThrHis TyrGlyGlnLysAlaIleLeuPheLeuProLeuProValSerSe
                                                                                             SacI
                                                                                             - - - - - -
           StuI                                          MlsI                           Ecl136II
           - - - - - -                                   - - - - - -                    - - - - - -
5401  AGGCCTTAAAAAAAAATGGTTCCTGTAAGCGTGGACCACGGACTCA CTATGGCCAAAAGGCTATCTTGTTCCTGCCACTACCAGTGAGCTC
      TCCGGAATTTTTTTTTACCAAGGACATTCGCACCTGGTGCCTGAGT GATACCGGTTTTCCGATAGAACAAGGACGGTGATGGTCACTCGAG
```

```
  +2 rAsp***
                       SalI
                       - - - - - -
              EcoRI SacI HindII         XmaIII        XhoI
              - - - - - - - - - - - -   - - - - - -   - - - - - -
       BamHI    Ecl136IIHincIIHindIII   NotI          AvaI
       - - - -  - - - - - - - - - - - - - - - - - - - - - - - - -
5491  CGACTAAGGATCCGAATTCGAGCTCCGTCGACAAGCTTGCGGCCG CACTCGAGCACCACCACCACCACCACTGAGATCCGGCTGCTAACA
      GCTGATTCCTAGGCTTAAGCTCGAGGCAGCTGTTCGAACGCCGGC GTGAGCTCGTGGTGGTGGTGGTGGTGACTCTAGGCCGACGATTGT
```

NUCLEOTIDE AND AMINO ACID SEQUENCE FOR CHEMICALLY SYNTHESIZED HUMAN A FGF (140 AMINO ACIDS)

FIG. 8

```
                                          BpiI
                                          ----
2971 GGGCGCTGACTTCCGCGTTTCCAGACTTTACGAAACACGGAAACC GAAGACCATTCATGTTGTTGCTCAGGTCGCAGACGTTTTGCAGCA
     CCCGCGACTGAAGGCGCAAAGGTCTGAAATGCTTTGTGCCTTTGG CTTCTGGTAAGTACAACAACGAGTCCAGCGTCTGCAAAACGTCGT

PpuMI
                                                                                    -------
                                                                                    EcoO109I
                                                                                    -------
                                                                                    DraII
                                                                                    -------
                                                                                    AvaII
                                                                                    -----
3061 GCAGTCGCTTCACGTTCGCTCGCGTATCGGTGATTCATTCTGCTA ACCAGTAAGGCAACCCCGCCAGCCTAGCCGGGTCCTCAACGACAG
     CGTCAGCGAAGTGCAAGCGAGCGCATAGCCACTAAGTAAGACGAT TGGTCATTCCGTTGGGGCGGTCGGATCGGCCCAGGAGTTGCTGTC

BsaBI
                        ---------
            NsbI        BglII              VspI      BfmI              MbiI
            ----        -----              ----      ----              ----
3151 GAGCACGATCATGCGCACCCGTGGGGCCGCCAGATCTCGATCCCG CGAAATTAATACGACTCACTATAGGGAATTGTGAGCGGATAACA
     CTCGTGCTAGTACGCGTGGGCACCCCGGCGGTCTAGAGCTAGGGC GCTTTAATTATGCTGAGTGATATCCCTTAACACTCGCCTATTGT
                                                              promoter      operator MetAlaGluGlyGluIleThrThrPheThrAlaLeuThrGl
 +2                                                                                   HpaI
                                                                                      ----
                                                                                      HindII
                                                                                      ------
            XbaI                               NdeI EcoS7I                            HincII
            ----                               ---- ------                            ------
3241 ATTCCCTCTAGAAATAATTTTGTTTAACTTTAAGAAGGAGATAT ACATATGGCTGAAGGGGAAATCACCACCTTTACAGCGTTAACGGA
     TAAGGGAGATCTTTATTAAAACAAATTGAAATTCTTCCTCTATA TGTATACCGACTTCCCCTTTAGTGGTGGAAATGTCGCAATTGCCT +2 uLysPheAsnLeuProProGlyAsnTyrLysLysProLysLeuLeu TyrCysSerAsnGlyGlyHisPheLeuArgIleLeuProAspGl
         SmaI                                        PstI
         ----                                        ----
         AvaI            HindIII         BfmI                               EcoRI
         ----            -------         ----                               -----
3331 GAAATTTAACCTTCCGCCCGGGAATTACAAAAAACCCAAGCTTCT TTACTGCAGTAACGGAGGACACTTCCTGCGAATTCTGCCAGATGG
     CTTTAAATTGGAAGGCGGGCCCTTAATGTTTTTTGGGTTCGAAGA AATGACGTCATTGCCTCCTGTGAAGGACGCTTAAGACGGTCTACC +2 yThrValAspGlyThrArgAspArgSerAspGlnHisIleGlnLeu GlnLeuSerAlaGluSerValGlyGluValTyrIleLysSerTh
                                                                                          SalI
                                                                                          ----
               PvuI                            XmaIII                                   HindII
               ----                            ------                                   ------
         NruI                  PvuII       CfrI                                         HincII
         ----                  -----       ----                                         ------
3421 CACAGTAGATGGGACTCGCGATCGCTCCGACCAGCACATTCAGCT GCAACTCTCGGCCGAAAGCGTTGGAGAGGTCTATATCAAGTCGAC
     GTGTCATCTACCCTGAGCGCTAGCGAGGCTGGTCGTGTAAGTCGA CGTTGAGAGCCGGCTTTCGCAACCTCTCCAGATATAGTTCAGCTG +2 rGluThrGlyGlnTyrLeuAlaMetAspThrAspGlyLeuLeuTyr·GlySerGlnThrProAsnGluGluCysLeuPheLeuGluArgLe
       MlsI RsaI         StyI
       ---- ----         ----
         CfrI Csp6I      NcoI                      AcyI           Mval269I        XbaI
         ---- -----      ----                      ----           --------        ----
3511 GGAGACTGGCCAGTACCTTGCCATGGACACCGATGGGCTTCTGTA TGGCTCACAGACGCCTAACGAAGAATGCTTGTTTCTAGAAAGACT
     CCTCTGACCGGTCATGGAACGGTACCTGTGGCTACCCGAAGACAT ACCGAGTGTCTGCGGATTGCTTCTTACGAACAAAGATCTTTCTGA
     BsmAI
     -----
```

NUCLEOTIDE AND AMINO ACID SEQUENCE FOR CHEMICALLY
SYNTHESIZED INTERFERONα−2B

FIG. 10

ELECTROPHOREGRAMM

1—MOLECULAR WEIGHT KIT (94 000, 67 000, 43 000, 30 000 20 100, 14 4000)

THE CULTURAL MEDIUM, CONTAINING:
2—haFGF 134(40μ l OF THE CULTURAL MEDIUM)
3—haFGF 140(40μ l OF THE CULTURAL MEDIUM)
4—IFNα2B(40μ l OF THE CULTURAL MEDIUM)
5—haFGF 155(40μ l OF THE CULTURAL MEDIUM)
6—HGH(40μ l OF THE CULTURAL MEDIUM)
7—MAP(40μ l OF THE CULTURAL MEDIUM)
8—β-GALACTOSIDASE OF E. COLI(40μ l OF THE CULTURAL MEDIUM)

ELECTROPHOREGRAMM OF THE PURIEFIED PRODUCTS:

1-MOLECULAR WEIGHT KIT (94 000,67 000,43 000,30 000
20 100, 14 4000)
2-haFGF 134
3-haFGF 140
4-haFGF 146
5-IFNα2B
6-haFGF 155
7-MAP
8-MOLECULAR WEIGHT KIT

SEQUENCE LISTING

```
<160> NUMBER OF SEQ ID NOS: 11

<210> SEQ ID NO 1
<211> LENGTH: 630
<212> TYPE: DNA
<213> ORGANISM: Artificial Sequence
<220> FEATURE:
<223> OTHER INFORMATION: This sequence was chemically synthesized based
      upon the amino acid sequence of human acidic fibroblast growth
      factor (155 amino acids) using codons which are used in highly
      expressed proteins from E. coli.
<221> NAME/KEY: CDS
<222> LOCATION: (122)...(590)

<400> SEQUENCE: 1
gcgtagagga tcgagatctc gatcccgcga aattaatacg actcactata gggggaattgt      60 gagcggataa caattcccct ctagaaataa ttttgtttaa ctttaagaag gagatataca     120 t atg gct gaa ggg gaa atc acc acc ttt aca gcg tta acg gag aaa ttt     169
  Met Ala Glu Gly Glu Ile Thr Thr Phe Thr Ala Leu Thr Glu Lys Phe
  1               5                   10                  15 aac ctt ccg ccc ggg aat tac aaa aaa ccc aag ctt ctt tac tgc agt       217
Asn Leu Pro Pro Gly Asn Tyr Lys Lys Pro Lys Leu Leu Tyr Cys Ser
                20                  25                  30 aac gga gga cac ttc ctg cga att ctg cca gat ggc aca gta gat ggg       265
Asn Gly Gly His Phe Leu Arg Ile Leu Pro Asp Gly Thr Val Asp Gly
            35                  40                  45 act cgc gat cgc tcc gac cag cac att cag ctg caa ctc tcg gcc gaa       313
Thr Arg Asp Arg Ser Asp Gln His Ile Gln Leu Gln Leu Ser Ala Glu
        50                  55                  60 agc gtt gga gag gtc tat atc aag tcg acg gag act ggc cag tac ctt       361
Ser Val Gly Glu Val Tyr Ile Lys Ser Thr Glu Thr Gly Gln Tyr Leu
65                  70                  75                  80 gcc atg gac acc gat ggg ctt ctg tat ggc tca cag acg cct aac gaa       409
```

-continued

```
Ala Met Asp Thr Asp Gly Leu Leu Tyr Gly Ser Gln Thr Pro Asn Glu
            85                  90                  95 gaa tgc ttg ttt cta gaa aga cta gaa gaa aac cat tac aac acg tac    457
Glu Cys Leu Phe Leu Glu Arg Leu Glu Glu Asn His Tyr Asn Thr Tyr
            100                 105                 110 ata tcg aaa aaa cat gca gag aag aac tgg ttt gta ggc ctt aaa aaa    505
Ile Ser Lys Lys His Ala Glu Lys Asn Trp Phe Val Gly Leu Lys Lys
        115                 120                 125 aat ggt tcc tgt aag cgt gga cca cgg act cac tat ggc caa aag gct    553
Asn Gly Ser Cys Lys Arg Gly Pro Arg Thr His Tyr Gly Gln Lys Ala
    130                 135                 140 atc ttg ttc ctg cca cta cca gtg agc tcc gac taa g gatccgaatt       600
Ile Leu Phe Leu Pro Leu Pro Val Ser Ser Asp  *
145                 150                 155 cgagctccgt cgacaagctt gcggccgcac                                   630
```

<210> SEQ ID NO 2
<211> LENGTH: 155
<212> TYPE: PRT
<213> ORGANISM: Homo sapiens

<400> SEQUENCE: 2

```
Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45

Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
            85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

<210> SEQ ID NO 3
<211> LENGTH: 468
<212> TYPE: DNA
<213> ORGANISM: Homo sapiens

<400> SEQUENCE: 3

```
atggctgaag ggaaatcac caccttcaca gccctgaccg agaagtttaa tctgcctcca      60
gggaattaca agaagcccaa actcctctac tgtagcaacg ggggccactt cctgaggatc    120
cttccggatg gcacagtgga tgggacaagg gacaggagcg accagcacat tcagctgcag    180
ctcagtgcgg aaagcgtggg ggaggtgtat ataaagagta ccgagactgg ccagtacttg    240
gccatggaca ccgacgggct tttatacggc tcacagacac caaatgagga atgtttgttc    300
ctggaaaggc tggaggagaa ccattacaac acctatatat ccaagaagca tgcagagaag    360
```

```
aattggtttg ttggcctcaa gaagaatggg agctgcaaac gcggtcctcg gactcactat    420
ggccagaaag caatcttgtt tctcccctg ccagtctctt ctgattaa                  468
```

<210> SEQ ID NO 4
<211> LENGTH: 630
<212> TYPE: DNA
<213> ORGANISM: Artificial Sequence
<220> FEATURE:
<223> OTHER INFORMATION: This sequence is a chemically synthesized
      sequence encoding a 134 amino acid form of fibroblast growth
      factor with alterations for preferred codon usage in E. coli
<221> NAME/KEY: CDS
<222> LOCATION: (122)...(526)

<400> SEQUENCE: 4

```
gcgtagagga tcgagatctc gatcccgcga aattaatacg actcactata ggggaattgt    60
gagcggataa caattcccct ctagaaataa ttttgtttaa ctttaagaag gagatataca   120 t atg aat tac aaa aaa ccc aag ctt ctt tac tgc agt aac gga gga cac   169
  Met Asn Tyr Lys Lys Pro Lys Leu Leu Tyr Cys Ser Asn Gly Gly His
   1               5                  10                  15 ttc ctg cga att ctg cca gat ggc aca gta gat ggg act cgc gat cgc     217
Phe Leu Arg Ile Leu Pro Asp Gly Thr Val Asp Gly Thr Arg Asp Arg
                 20                  25                  30 tcc gac cag cac att cag ctg caa ctc tcg gcc gaa agc gtt gga gag     265
Ser Asp Gln His Ile Gln Leu Gln Leu Ser Ala Glu Ser Val Gly Glu
             35                  40                  45 gtc tat atc aag tcg acg gag act ggc cag tac ctt gcc atg gac acc     313
Val Tyr Ile Lys Ser Thr Glu Thr Gly Gln Tyr Leu Ala Met Asp Thr
     50                  55                  60 gat ggg ctt ctg tat ggc tca cag acg cct aac gaa gaa tgc ttg ttt     361
Asp Gly Leu Leu Tyr Gly Ser Gln Thr Pro Asn Glu Glu Cys Leu Phe
 65                  70                  75                  80 cta gaa aga cta gaa gaa aac cat tac aac acg tac ata tcg aaa aaa     409
Leu Glu Arg Leu Glu Glu Asn His Tyr Asn Thr Tyr Ile Ser Lys Lys
                 85                  90                  95 cat gca gag aag aac tgg ttt gta ggc ctt aaa aaa aat ggt tcc tgt     457
His Ala Glu Lys Asn Trp Phe Val Gly Leu Lys Lys Asn Gly Ser Cys
                100                 105                 110 aag cgt gga cca cgg act cac tat ggc caa aag gct atc ttg ttc ctg     505
Lys Arg Gly Pro Arg Thr His Tyr Gly Gln Lys Ala Ile Leu Phe Leu
            115                 120                 125 cca cta cca gtg agc tcc gac taaggatccg aattcgagct ccgtcgacaa        556
Pro Leu Pro Val Ser Ser Asp
            130             135 gcttgcggcc gcactcgagc accaccacca ccaccactga gatccggctg ctaacaaagc   616
ccgaaaggaa gctg                                                     630
```

<210> SEQ ID NO 5
<211> LENGTH: 135
<212> TYPE: PRT
<213> ORGANISM: Homo sapiens
<220> FEATURE:
<223> OTHER INFORMATION: Translated protein sequence for the chemically
      synthesized 134 amino acid form of fibroblast growth factor

<400> SEQUENCE: 5

```
Met Asn Tyr Lys Lys Pro Lys Leu Leu Tyr Cys Ser Asn Gly Gly His
 1               5                  10                  15

Phe Leu Arg Ile Leu Pro Asp Gly Thr Val Asp Gly Thr Arg Asp Arg
             20                  25                  30
```

```
Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
 50                  55                  60

Asp Gly Leu Leu Tyr Gly Ser Gln Thr Pro Asn Glu Glu Cys Leu Phe
 65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
        115                 120                 125

Pro Leu Pro Val Ser Ser Asp
        130                 135

<210> SEQ ID NO 6
<211> LENGTH: 630
<212> TYPE: DNA
<213> ORGANISM: Artificial Sequence
<220> FEATURE:
<223> OTHER INFORMATION: This sequence is a chemically synthesized
      sequence encoding a 140 amino acid form of fibroblast growth
      factor with alterations for preferred codon usage in E. coli
<221> NAME/KEY: CDS
<222> LOCATION: (122)...(544)

<400> SEQUENCE: 6
gcgtagagga tcgagatctc gatcccgcga aattaatacg actcactata ggggaattgt     60
gagcggataa caattcccct ctagaaataa ttttgtttaa ctttaagaag gagatataca    120 t atg ttt aac ctt ccg ccc ggg aat tac aaa aaa ccc aag ctt ctt tac    169
  Met Phe Asn Leu Pro Pro Gly Asn Tyr Lys Lys Pro Lys Leu Leu Tyr
   1               5                  10                  15 tgc agt aac gga gga cac ttc ctg cga att ctg cca gat ggc aca gta    217
Cys Ser Asn Gly Gly His Phe Leu Arg Ile Leu Pro Asp Gly Thr Val
                20                  25                  30 gat ggg act cgc gat cgc tcc gac cag cac att cag ctg caa ctc tcg    265
Asp Gly Thr Arg Asp Arg Ser Asp Gln His Ile Gln Leu Gln Leu Ser
         35                  40                  45 gcc gaa agc gtt gga gag gtc tat atc aag tcg acg gag act ggc cag    313
Ala Glu Ser Val Gly Glu Val Tyr Ile Lys Ser Thr Glu Thr Gly Gln
     50                  55                  60 tac ctt gcc atg gac acc gat ggg ctt ctg tat ggc tca cag acg cct    361
Tyr Leu Ala Met Asp Thr Asp Gly Leu Leu Tyr Gly Ser Gln Thr Pro
 65                  70                  75                  80 aac gaa gaa tgc ttg ttt cta gaa aga cta gaa gaa aac cat tac aac    409
Asn Glu Glu Cys Leu Phe Leu Glu Arg Leu Glu Glu Asn His Tyr Asn
                85                  90                  95 acg tac ata tcg aaa aaa cat gca gag aag aac tgg ttt gta ggc ctt    457
Thr Tyr Ile Ser Lys Lys His Ala Glu Lys Asn Trp Phe Val Gly Leu
            100                 105                 110 aaa aaa aat ggt tcc tgt aag cgt gga cca cgg act cac tat ggc caa    505
Lys Lys Asn Gly Ser Cys Lys Arg Gly Pro Arg Thr His Tyr Gly Gln
        115                 120                 125 aag gct atc ttg ttc ctg cca cta cca gtg agc tcc gac taaggatccg    554
Lys Ala Ile Leu Phe Leu Pro Leu Pro Val Ser Ser Asp
    130                 135                 140 aattcgagct ccgtcgacaa gcttgcggcc gcactcgagc accaccacca ccaccactga    614
gatccggctg ctaaca                                                    630
```

<210> SEQ ID NO 7
<211> LENGTH: 141
<212> TYPE: PRT
<213> ORGANISM: Homo sapiens
<220> FEATURE:
<223> OTHER INFORMATION: Translated protein sequence for the chemically synthesized 140 amino acid form of fibroblast growth factor

<400> SEQUENCE: 7

```
Met Phe Asn Leu Pro Pro Gly Asn Tyr Lys Pro Lys Leu Leu Tyr
 1               5                  10                  15

Cys Ser Asn Gly Gly His Phe Leu Arg Ile Leu Pro Asp Gly Thr Val
            20                  25                  30

Asp Gly Thr Arg Asp Arg Ser Asp Gln His Ile Gln Leu Gln Leu Ser
        35                  40                  45

Ala Glu Ser Val Gly Glu Val Tyr Ile Lys Ser Thr Glu Thr Gly Gln
    50                  55                  60

Tyr Leu Ala Met Asp Thr Asp Gly Leu Leu Tyr Gly Ser Gln Thr Pro
65                  70                  75                  80

Asn Glu Glu Cys Leu Phe Leu Glu Arg Leu Glu Glu Asn His Tyr Asn
                85                  90                  95

Thr Tyr Ile Ser Lys Lys His Ala Glu Lys Asn Trp Phe Val Gly Leu
            100                 105                 110

Lys Lys Asn Gly Ser Cys Lys Arg Gly Pro Arg Thr His Tyr Gly Gln
        115                 120                 125

Lys Ala Ile Leu Phe Leu Pro Leu Pro Val Ser Ser Asp
    130                 135                 140
```

<210> SEQ ID NO 8
<211> LENGTH: 1822
<212> TYPE: DNA
<213> ORGANISM: Artificial Sequence
<220> FEATURE:
<221> NAME/KEY: TATA_signal
<222> LOCATION: (102)...(107)
<221> NAME/KEY: CDS
<222> LOCATION: (193)...(202)
<221> NAME/KEY: intron
<222> LOCATION: (203)...(458)
<221> NAME/KEY: CDS
<222> LOCATION: (459)...(619)
<221> NAME/KEY: intron
<222> LOCATION: (620)...(828)
<221> NAME/KEY: CDS
<222> LOCATION: (829)...(948)
<221> NAME/KEY: intron
<222> LOCATION: (949)...(1041)
<221> NAME/KEY: CDS
<222> LOCATION: (1042)...(1206)
<221> NAME/KEY: intron
<222> LOCATION: (1207)...(1459)
<221> NAME/KEY: CDS
<222> LOCATION: (1460)...(1654)
<223> OTHER INFORMATION: Chemically synthesized sequence for Human Growth Hormone using codons preferred for expression in E. coli

<400> SEQUENCE: 8

```
ggagcttcta aattatccat tagcacaagc ccgtcagtgg ccccatgcat aaatgtacac      60
agaaacaggt gggggcaaca gtgggagaga aggggccagg gtataaaaag ggcccacaag     120
agaccggctc aaggatccca aggcccaact ccccgaacca ctcagggtcc tgtgacgct      180 cacctagctg ca atg gct aca g gtaagcgccc ctaaaatccc tttgggcaca          232
              Met Ala Thr
                1 atgtgtcctg aggggagagg cagcgacctg tagatgggac gggggcacta accctcaggt    292
```

```
ttggggcttc tgaatgagta tcgccatgta agcccagtat ggccaatctc agaaagctcc      352
tggtccctgg agggatggag agagaaaaac aaacagctcc tggagcaggg agagtgctgg      412
cctcttgctc tccggctccc tctgttgccc tctggtttct ccccag gc tcc cgg acg     469
                                                    Gly Ser Arg Thr
                                                                 5 tcc ctg ctc ctg gct ttt ggc ctg ctc tgc ctg ccc tgg ctt caa gag       517
Ser Leu Leu Leu Ala Phe Gly Leu Leu Cys Leu Pro Trp Leu Gln Glu
         10                  15                  20 ggc agt gcc ttc cca acc att ccc tta tcc agg ctt ttt gac aac gct       565
Gly Ser Ala Phe Pro Thr Ile Pro Leu Ser Arg Leu Phe Asp Asn Ala
     25                  30                  35 atg ctc cgc gcc cat cgt ctg cac cag ctg gcc ttt gac acc tac cag       613
Met Leu Arg Ala His Arg Leu His Gln Leu Ala Phe Asp Thr Tyr Gln
 40                  45                  50                  55 gag ttt gtaagctctt ggggaatggg tgcgcatcag gggtggcagg aagggtgac         669
Glu Phe tttccccgc tgggaaataa gaggaggaga ctaaggagct cagggttttt cccgaagcga      729
aaatgcaggc agatgagcac acgctgagtg aggttcccag aaaagtaaca atgggagctg     789
gtctccagcg tagaccttgg tgggcggtcc ttctcctag gaa gaa gcc tat atc        843
                                            Glu Glu Ala Tyr Ile
                                                             60 cca aag gaa cag aag tat tca ttc ctg cag aac ccc cag acc tcc ctc       891
Pro Lys Glu Gln Lys Tyr Ser Phe Leu Gln Asn Pro Gln Thr Ser Leu
         65                  70                  75 tgt ttc tca gag tct att ccg aca ccc tcc aac agg gag gaa aca caa       939
Cys Phe Ser Glu Ser Ile Pro Thr Pro Ser Asn Arg Glu Glu Thr Gln
 80                  85                  90 cag aaa tcc gtgagtggat gccttgaccc caggcgggga tgggggagac                988
Gln Lys Ser
 95 ctgtagtcag agcccccggg cagcacaggc caatgcccgt ccttcccctg cag aac        1044
                                                             Asn cta gag ctg ctc cgc atc tcc ctg ctc ctc atc cag tcg tgg ctg gag       1092
Leu Glu Leu Leu Arg Ile Ser Leu Leu Leu Ile Gln Ser Trp Leu Glu
         100                 105                 110 ccc gtg cag ttc ctc agg agt gtc ttc gcc aac agc ctg gtg tac ggc       1140
Pro Val Gln Phe Leu Arg Ser Val Phe Ala Asn Ser Leu Val Tyr Gly
115                 120                 125                 130 gcc tct gac agc aac gtc tat gac ctc cta aag gac cta gag gaa ggc       1188
Ala Ser Asp Ser Asn Val Tyr Asp Leu Leu Lys Asp Leu Glu Glu Gly
                 135                 140                 145 atc caa acg ctg atg ggg gtggggtgg cgctaggggt ccccaatctt                1236
Ile Gln Thr Leu Met Gly
             150 ggagccccac tgactttgag agctgtgtta gagaaacact gctgccctct ttttagcagt     1296 ccaggccctg acccaagaga actcaccttta ttcttcattt ccctcgtga atcctctagc     1356 ctttctctac accctgaagg ggaggagga aaatgaatga atgagaaagg gagggagcag      1416 tacccaagcg cttggcctct ccttctcttc cttcactttg cag agg ctg gaa gat      1471
                                                Arg Leu Glu Asp
                                                             155 ggc agc ccc cgg act ggg cag atc ttc aag cag acc tac agc aag ttc       1519
Gly Ser Pro Arg Thr Gly Gln Ile Phe Lys Gln Thr Tyr Ser Lys Phe
             160                 165                 170 gac aca aac tca cac aac gat gac gca cta ctc aag aac tac ggg ctg       1567
Asp Thr Asn Ser His Asn Asp Asp Ala Leu Leu Lys Asn Tyr Gly Leu
```

-continued

```
                175                 180                 185
ctc tac tgc ttc agg aag gac atg gac aag gtc gag aca ttc ctg cgc    1615
Leu Tyr Cys Phe Arg Lys Asp Met Asp Lys Val Glu Thr Phe Leu Arg
    190                 195                 200 atc gtg cag tgc cgc tct gtg gag ggc agc tgt ggc ttc tagctgccg      1664
Ile Val Gln Cys Arg Ser Val Glu Gly Ser Cys Gly Phe
205                 210                 215 ggtggcatcc ctgtgacccc tccccagtgc ctctcctggc cttggaagtt gccactccag    1724
tgcccaccag ccttgtccta ataaaattaa gttgcatcat tttgtctgac taggtgtcct    1784
ctataatatt atggggtgga gggggtggt ttggagca                             1822
```

<210> SEQ ID NO 9
<211> LENGTH: 217
<212> TYPE: PRT
<213> ORGANISM: Homo sapiens

<400> SEQUENCE: 9

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 10
<211> LENGTH: 990
<212> TYPE: DNA
<213> ORGANISM: Artificial Sequence
<220> FEATURE:
<223> OTHER INFORMATION: Chemically synthesized sequence for human
      interferon alpha- 2b
<221> NAME/KEY: promoter
<222> LOCATION: (231)...(249)
<221> NAME/KEY: CDS
<222> LOCATION: (320)...(784)

```
<400> SEQUENCE: 10
gggcgctgac ttccgcgttt ccagacttta cgaaacacgg aaaccgaaga ccattcatgt      60
tgttgctcag gtcgcagacg ttttgcagca gcagtcgctt cacgttcgct cgcgtatcgg     120
tgattcattc tgctaaccag taaggcaacc ccgccagcct agccgggtcc tcaacgacag     180
gagcacgatc atgcgcaccc gtggggccgc cagatctcga tcccgcgaaa ttaatacgac     240
tcactatagg ggaattgtga gcggataaca attcccctct agaataatt ttgtttaact     300 ttaagaagga gatatacat atg gct gaa ggg gaa atc acc acc ttt aca gcg     352
                     Met Ala Glu Gly Glu Ile Thr Thr Phe Thr Ala
                      1               5                  10 tta acg gag aaa ttt aac ctt ccg ccc ggg aat tac aaa aaa ccc aag      400
Leu Thr Glu Lys Phe Asn Leu Pro Pro Gly Asn Tyr Lys Lys Pro Lys
            15                  20                  25 ctt ctt tac tgc agt aac gga gga cac ttc ctg cga att ctg cca gat      448
Leu Leu Tyr Cys Ser Asn Gly Gly His Phe Leu Arg Ile Leu Pro Asp
        30                  35                  40 ggc aca gta gat ggg act cgc gat cgc tcc gac cag cac att cag ctg      496
Gly Thr Val Asp Gly Thr Arg Asp Arg Ser Asp Gln His Ile Gln Leu
    45                  50                  55 caa ctc tcg gcc gaa agc gtt gga gag gtc tat atc aag tcg acg gag      544
Gln Leu Ser Ala Glu Ser Val Gly Glu Val Tyr Ile Lys Ser Thr Glu
60                  65                  70                  75 act ggc cag tac ctt gcc atg gac acc gat ggg ctt ctg tat ggc tca      592
Thr Gly Gln Tyr Leu Ala Met Asp Thr Asp Gly Leu Leu Tyr Gly Ser
                80                  85                  90 cag acg cct aac gaa gaa tgc ttg ttt cta gaa aga cta gaa gaa aac      640
Gln Thr Pro Asn Glu Glu Cys Leu Phe Leu Glu Arg Leu Glu Glu Asn
            95                  100                 105 cat tac aac acg tac ata tcg aaa aaa cat gca gag aag aac tgg ttt      688
His Tyr Asn Thr Tyr Ile Ser Lys Lys His Ala Glu Lys Asn Trp Phe
        110                 115                 120 gta ggc ctt aaa aaa aat ggt tcc tgt aag cgt gga cca cgg act cac      736
Val Gly Leu Lys Lys Asn Gly Ser Cys Lys Arg Gly Pro Arg Thr His
    125                 130                 135 tat ggc caa aag gct atc ttg ttc ctg cca cta cca gtg agc tcc gac      784
Tyr Gly Gln Lys Ala Ile Leu Phe Leu Pro Leu Pro Val Ser Ser Asp
140                 145                 150                 155 taaggatccg aattcgagct ccgtcgacaa gcttgcggcc gcactcgagc accaccaca     844 ccaccactga gatccggctg ctaacaaagc ccgaaaggaa gctgagttgg ctgctgccac     904
cgctgagcaa taactagcat aaccccttgg ggcctctaaa cgggtcttga ggggttttt     964 gctgaaagga ggaactatat ccggat                                          990

<210> SEQ ID NO 11
<211> LENGTH: 155
<212> TYPE: PRT
<213> ORGANISM: Homo sapiens
<220> FEATURE:
<223> OTHER INFORMATION: Translated protein sequence for the chemically
      synthesized human interferon alpha-2b

<400> SEQUENCE: 11

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
            20                  25                  30

Asn Gly Gly His Phe Leu Arg Ile Leu Pro Asp Gly Thr Val Asp Gly
        35                  40                  45
```

-continued

```
Thr Arg Asp Arg Ser Asp Gln His Ile Gln Leu Gln Leu Ser Ala Glu
    50                  55                  60

Ser Val Gly Glu Val Tyr Ile Lys Ser Thr Glu Thr Gly Gln Tyr Leu
65                  70                  75                  80

Ala Met Asp Thr Asp Gly Leu Leu Tyr Gly Ser Gln Thr Pro Asn Glu
            85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155
```

PHAGE-DEPENDENT SUPERPRODUCTION OF BIOLOGICALLY ACTIVE PROTEIN AND PEPTIDES

RELATED APPLICATION

The present application claims priority to provisional patent application Ser. No. 60/225,437, entitled, "Phage-Dependent Superproduction of Biologically Active Protein and Peptides," filed on Aug. 15, 2000.

BACKGROUND OF THE INVENTION

1. Field of the Invention

This invention relates to recombinant DNA technology and more particularly to a new method for enhancing the production of heterologous proteins in bacterial host cells. The disclosed method involves infecting host cells, which contain plasmid encoding the gene of interest operably linked to the T7 promoter, with bacteriophage λ to induce lysis of the bacterial host cells. Super-production may be achieved in selected host cells either when the plasmid alone carries at least one copy of the heterologous DNA or when both plasmid and phage λ each carry at least one copy of the heterologous DNA.

2. Description of the Related Art

At present, genetic engineering methods allow creating microorganism strains capable of producing substantial amounts of various bioactive substances having important applications in medicine and industry. Typically, plasmid vectors into which a heterologous gene has been inserted are used to transform bacterial host cells. Different strains of *E. coli* are frequently used as recipient cells. Using such plasmid-dependent transformation methods, *E. coli* cells have been engineered to produce a variety of valuable human peptides and proteins, including insulin, γ-interferon, a number of interleukins, superoxidedismutase, plasminogen activator, tumor necrosis factor, erythropoietin, etc. These substances are either already used in medical practice or undergoing different stages of clinical studies.

However, the plasmid method has serious disadvantages. It is technologically complicated, since the desired product has to be extracted from bacterial cells after biosynthesis, which is a multi-stage process. For example, interferon extraction involves disintegration of cells, buffer extraction, polyethylemenin processing, illumination, sedimentation by ammonium sulfate, dialysis, and centrifugation (Goeddel, EP 0043980). The necessity for such extraction and purification steps not only complicates production technology of the recombinant product, but also results in substantial losses, especially during large-scale industrial production.

A further complicating factor is that at relatively high levels of expression of the cloned genes, the eukaryotic proteins generated tend to accumulate in the cytoplasm of *E. coli* as insoluble aggregates, which are often associated with cell membranes. Consequently, the already difficult extraction and purification methods discussed above should be supplemented with additional technical procedures related to the extraction of the insoluble inclusion bodies. Usually, the insoluble proteins are solubilized using ionic detergents, such as SDS or laurylsarcosine, at increased temperatures or in the presence of denaturants, such as 8 M urea or 6–8 M guanidine-HCl.

Often, the final stage of purification involves renaturation and reoxidation of the solubilized polypeptides, which is required to restore functional activity. Disulfide bonds, which are necessary for proper folding of the protein in its native conformation, should be reformed. Renaturation procedures, such as disulfide interchange, may use expensive and relatively toxic reagents, like glutathione, and oxidized 2-mercaptoethanol or dithiothreitol. Further, the final yield of bioactive genetically-engineered proteins may be relatively low. Moreover, the presence of even trace concentrations of the toxic reagents needed to solubilize and then re-establish secondary and tertiary protein structure may prohibit subsequent clinical application of the proteins. Thus, the generation of targeted protein in the form of insoluble inclusion bodies within the bacterial host cells not only complicates the production of recombinant proteins and results in diminished yield, but may also render the final protein unsuitable for clinical use (Fisher, B., Sumner, I., Goodenough, P. Biotech. and Bioeng. 41:3–13, 1993).

The technological difficulties associated with the extraction of proteins produced by the expression of heterologous genes from plasmid-transformed bacterial host cells may be overcome by infecting the transformed bacterial host cells with bacteriophage, whose lytic pathway results in lysis of the bearer cell. Thus, the desired protein may be simply released into the culture medium (Breeze A. S. GB 2 143 238A). Accordingly, Breeze disclosed a method of increasing the yield of enzyme produced in *E. coli* by infecting the bacterial cells with phage λ carrying a temperature-sensitive mutation in cI to provide controlled lysis. The cI-gene product is a repressor of early transcription and consequently blocks transcription of the late region of the phage DNA, which is required for head and tail assembly and cell lysis (Mantiatis, T., Fritsch, E. F., Sambrook, J., MOLECULAR CLONING: A LABORATORY MANUAL, 1982, Cold Spring Harbor Laboratory Press). Bacteriophages carrying a temperature-sensitive mutation in cI are able to establish and maintain the lysogenic state as long as the cells are propagated at a temperature that allows the cI-gene product to repress transcription of phage genes necessary for lytic growth. Accordingly, the transformed bacterial host cells may be cultivated at 30° C., wherein the cI-mediated suppression of phage DNA transcription continues and the phage remains in the lysogenic state, until the stage of maximum ferment production is reached. Subsequently, the culture temperature may be increased to 42° C. for 30 minutes in order to inactivate the cI repressor and permit the phage to begin its lytic development. The host cells may then be incubated for 2–3 hours at 30° C. to allow complete lysis and release of the enzyme (Breeze A. S. GB 2 143 238A).

Although Breeze teaches release of proteins from bacterial producer cells, it requires cultivating producers at temperatures not exceeding 30° C., which is not the optimum temperature for growth of *E. coli* cells. Synthesis at the optimum temperature (37° C.) is not possible, since cells at temperatures exceeding 32° C. undergo lysis before reaching the stage of maximum ferment accumulation due to the development of temperature-sensitive lytic prophage. Furthermore, incubation of the bacterial host cells at 42° C. for 30 min as disclosed by Breeze may activate proteases that destroy the targeted protein.

Auerbach et al. (U.S. Pat. No. 4,637,980) used a phage λ DNA fragment for inducing lytic release of recombinant products. In that method, like Breeze, the temperature-sensitive mutation in λ cI-gene product was used to provide temperature-dependent lysis of the bacterial host cells. The λ DNA fragment in Auerbach maintained functional endolysin-encoding genes, N, Q, R and S, for producing lysozyme following inactivation of the cI repressor at 42° C. Most of the remaining phage genes were deleted; mutations in O and P genes prevented replication of the phage DNA.

Consequently, the λ DNA was not a fully functional phage, capable of modulating expression of the targeted gene. Moreover, the λ DNA of Auerbach was not suitable for use as a vector for carrying targeted genes. Further, as discussed above, incubation of the bacterial host cells at 42° to 44° C. for 90–120 min as disclosed by Auerbach may activate proteases that destroy the targeted protein.

In addition to providing for the lytic release of intact protein from bacterial producer cells, bacteriophages have also been used as an alternative to bacterial plasmid-based vectors, for carrying heterologous DNA into host bacterial cells. (Murray, N. E. and Murray, K., Nature 251:476–481, 1974; Moir, A., Brammar, W. J., Molec. gen. Genet. 149:87–99, 1976). Typically, amplification of genes and their products is achieved during lytic growth of the phage, wherein the phage genome is integrated into the bacterial host DNA (Panasenko, S. M., Cameron, J. R., Davis, R. V., Lehman, L. E., Science 196:188–189, 1977; Murray, N. E. and Kelley, W. S., Molec. Gen. Genet. 175:77–87, 1979; Walter, F., Siegel, M., Malke, H., 1990, DD 276,694; Mory, Y., Revel, M., Chen, L., Sheldon, I. F., Yuti-Chernajovsky, 1983, GB 2,103,222A). Usually, either lysogenic cultures of recombinant phage λ are used for infecting the bacterial host cells, or "warmed up" bacterial cultures, already harboring recombinant lysogenic phage λ, are grown up to amplify expression of the heterologous genes.

Although there are examples of the successful use of λ vectors for expression of heterologous genes, λ vectors have been used primarily for gene cloning. Once cloned, the genes are transferred to plasmid vectors for more effective expression. For example, when E. coli is infected by phage λ Charon 4A C15, containing the human β-interferon gene, the quantity of interferon in cell lysate constituted 7–8×10$^6$ units/liter. After the DNA fragment bearing targeted gene was recloned from phage to plasmid, β-interferon yield increased to 1×10$^8$ units/liter (Moir, A., Brammar, W. J., Molec. gen. Genet. 149:87–99, 1976).

To increase the yield of heterologous protein generated in bacterial host cells by recombinant λ vectors, mutations in the phage genome have been introduced that cause phage λ to lose its ability to initiate bacterial cell lysis. Enhanced yield is thereby achieved by extending the period of time during which the heterologous gene is expressed by the bacterial host cells. Thus, for example, the yield of DNA ligase 1 in lysogenic cultures containing λ gt4ligS prophage, with amber-mutation in the S gene, was five times greater than the yield of DNA ligase 1 in lysogenic cultures containing λ gt4lig prophage without the amber-mutation (Panasenko, S. M., Cameron, J. R., Davis, R. V., Lehman, L. R., Science 196:188–189, 1977). The phage λ S protein is required for lysis; therefore S$^-$ mutants accumulate large numbers of intracellular progeny phage particles, as well as the targeted protein, without lysing the host cells (Mantiatis, T., Fritsch, E. F., Sambrook, J., MOLECULAR CLONING: A LABORATORY MANUAL, 1982, Cold Spring Harbor Laboratory Press).

Similar increases in the yield of DNA polymerase 1 were reported for lysogenic cultures containing recombinant phage λ with amber-mutations in the S and Q genes, compared to recombinant phage λ without the amber-mutations (Murray, N. E. and Kelley, W. S., Molec. gen. Genet. 175:77–87, 1979). The phage λ Q protein is required for transcription of the late region of the phage DNA, which includes many genes involved in head and tail assembly and cell lysis. (Mantiatis, T., Fritsch, E. F., Sambrook, J., MOLECULAR CLONING: A LABORATORY MANUAL, 1982, Cold Spring Harbor Laboratory Press).

In U.S. Pat. No. 4,710,463, Murray discloses lysogenizing a non-suppressing (Su°) strain of E. coli with phage λ containing the temperature-sensitive mutation in cI, as well as mutations in λ S and E genes. Consequently, prolonged cultivation of the lysogenic E. coli at 37° C. leads to high levels of production of the recombinant protein, which is retained within the cells, since these are not lysed by phage gene products in the normal way, and since the recombinant phage genome is not encapisdated, it remains available for transcription.

Despite the enhanced yield of heterologous proteins possible using λ-vectors with N, R, S, Q and/or E mutations, the potential technical advantages of bacteriophage vectors related to the lytic release of targeted proteins, may be lost with these mutations, because the targeted proteins accumulate inside the bacterial cell. Thus, when a lysis-defective mutant λ-vector is used for production of heterologous protein, the extraction and purification steps, discussed above for bacterial cells transformed by plasmid vectors, along with the resultant losses, should be performed.

The T7 promoter/T7 RNA polymerase system is useful for high level expression of recombinant proteins. The use of the T7 promoter requires the presence of T7 RNA polymerase. The T7 RNA polymerase may be supplied by induction of a recombinant T7 polymerase gene contained on a λ lysogen in the host strain or by transformation with a plasmid for expression of the T7 polymerase gene. The T7 RNA polymerase is very specific for its own promoter. Transcription reactions from the T7 promoter are very efficient and many copies of full length RNA can be produced from each template.

SUMMARY OF THE INVENTION

In one embodiment, a method for producing a biologically active protein is disclosed, including the steps of:

transforming a strain of E. coli with a plasmid having at least one copy of an expressible gene encoding a biologically active protein, operably linked to a T7 polymerase promoter, wherein the E. coli strain is capable of expressing the gene for T7 RNA polymerase;

infecting the transformed bacterial host cell with a bacteriophage λ capable of mediating delayed lysis; and cultivating the E. coli host cell under a culture condition that induces lytic growth of said cell without lysis until a desired level of production of said protein is reached, wherein said protein is produced as a soluble, biologically-active protein.

In a preferred embodiment, the bacteriophage λ has a temperature-sensitive mutation. In a more preferred embodiment, the temperature-sensitive mutation is cI$_{857}$. Preferably, the E. coli host cells are grown at a temperature which prevents lytic growth of the bacteriophage λ, prior to the cultivating step.

In a preferred embodiment, the bacteriophage λ has a mutation in at least one gene capable of mediating delayed lysis. In a more preferred embodiment, the at least one gene capable of mediating delayed lysis is selected from the group consisting of N, Q and R.

In a preferred embodiment, the strain of E. coli produces a suppressor for the repair of amber-mutations.

In a alternate embodiment, the strain of E. coli lacks a suppressor for the repair of amber-mutations.

In a preferred embodiment, the infecting bacteriophage λ is provided at a multiplicity of infection in a range of about 1 to about 100. In a more preferred embodiment, the infecting bacteriophage λ is provided at a multiplicity of infection in a range of about 10 to about 25.

Preferably, the bacteriophage-mediated delayed lysis of the strain of *E. coli* is delayed at higher multiplicities of infection relative to lower multiplicities of infection.

In one embodiment, the expressible gene encodes a human acidic fibroblast growth factor. In one alternate embodiment, the human acidic fibroblast growth factor contains 134 amino acids. In another alternate embodiment, the human acidic fibroblast growth factor contains 140 amino acids. In another alternate embodiment, the human acidic fibroblast growth factor contains 146 amino acids. In another alternate embodiment, the human acidic fibroblast growth factor contains 155 amino acids. In a most preferred embodiment, the human acidic fibroblast growth factor has the sequence as set forth in SEQ ID NO: 1.

In one embodiment, the expressible gene encodes a human growth hormone. In an alternate embodiment, the expressible gene encodes a human interferon. In yet another embodiment, the expressible gene encodes an *E. coli* methionine amino peptidase.

In a preferred embodiment, the gene for T7 RNA polymerase is under the control of an inducible promoter. In a more preferred embodiment, the inducible promoter is a lac UV 5 promoter.

In a preferred embodiment, a method of producing a biologically active protein is provided which includes the steps of:

a) growing a first strain of *E. coli* cells, which harbor a strain of bacteriophage λ, wherein the bacteriophage λ has a temperature-sensitive mutation, b) adjusting the temperature to provide for lysis of the first strain of *E. coli* cells and release of the bacteriophage λ, c) providing a second strain of *E. coli* cells which have been transformed with a plasmid having at least one copy of an expressible gene encoding said biologically active protein, said expressible gene being operably linked to a T7 polymerase promoter under the control of an inducible promoter, wherein the second strain of *E. coli* cells may be induced to express the gene for T7 RNA polymerase by addition of an inducer;

d) infecting the second strain of *E.coli* cells with the bacteriophage λ released from the first strain of *E. coli* cells; and e) incubating the infected second strain of *E. coli* cells in a culture medium containing the inducer, such that protein is produced and released into the culture medium upon lysis of the second strain of *E. coli* cells, wherein said protein is produced as a soluble, biologically-active protein at a concentration greater than 100 microgram/ml.

Also embodied within the presently disclosed invention is a chemically synthesized nucleic acid consisting essentially of the sequence set forth in SEQ ID NO: 1.

For purposes of summarizing the invention and the advantages achieved over the prior art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other feature of this invention will now be described with reference to the drawings of preferred embodiments which are intended to illustrate and not to limit the invention.

FIG. 1 shows the chemically synthesized nucleotide sequence for human acidic fibroblast growth factor (155 amino acids) (SEQ ID NO: 1) which has been modified by substitution of naturally occurring codons with codons found in highly expressed *E. coli* proteins and the translated amino acid sequence (SEQ ID NO: 2).

FIG. 2 shows the modifications made in the chemically synthesized haFGF 155 codons. FGF fr HUMECGFB is the sequence obtained from GenBank (at NCBI) (SEQ ID NO: 3). HaFGF 155 is the chemically synthesized sequence in accordance with one embodiment of the present invention (SEQ ID NO: 1).

FIG. 6 shows the chemically synthesized nucleotide sequence for human acidic fibroblast growth factor (134 amino acids) (SEQ ID NO: 4) which has been modified by substitution of naturally occurring codons with codons found in highly expressed *E. coli* proteins and the translated amino acid sequence (SEQ ID NO: 5).

FIG. 8 shows the chemically synthesized nucleotide sequence for human acidic fibroblast growth factor (140 amino acids) (SEQ ID NO: 6) which has been modified by substitution of naturally occurring codons with codons found in highly expressed *E. coli* proteins and the translated amino acid sequence (SEQ ID NO: 7).

FIG. 10 shows the chemically synthesized nucleotide sequence for human interferon α-2b (SEQ ID NO: 10) which has been modified by substitution of naturally occurring codons with codons found in highly expressed *E. coli* proteins and the translated amino acid sequence (SEQ ID NO: 11).

lane 5, 40 μl of culture media containing recombinant FGF 155 protein; lane 6, 40 μl of culture media containing recombinant human growth hormone; lane 7, 40 μl of culture media containing recombinant methionine aminopeptidase; lane 8, 40 μl of culture media containing β-galactosidase of E. coli.

Figure 12:
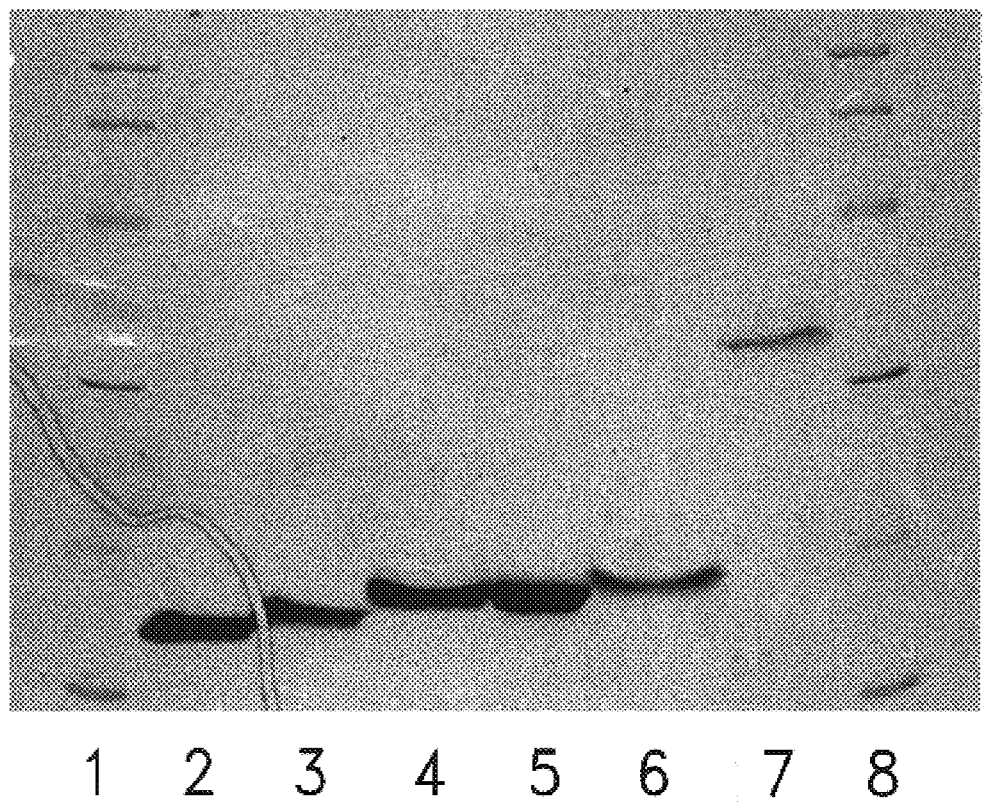

FIG. 12 shows a 12.5% SDS polyacrylamide gel containing recombinant proteins purified according to the presently claimed invention: lane 1, molecular weight standards; lane 2, 5 μg of purified FGF 134 protein; lane 3, 5 μg of purified FGF 140 protein; lane 4, 5 μg of purified FGF 146 protein; lane 5, 5 μg of purified interferon α2B protein; lane 6, 5 μg of purified FGF 155 protein; lane 7, 5 μg of purified methionine amino peptidase protein; lane 8, molecular weight standards.

DETAILED DESCRIPTION OF THE PREFERRED EMBODIMENT

While the described embodiment represents the preferred embodiment of the present invention, it is to be understood that modifications will occur to those skilled in the art without departing from the spirit of the invention. The scope of the invention is therefore to be determined solely by the appended claims.

Bacteriophage λ is useful as a vector because more than 40% of the viral genome is not essential for lytic growth. This area of the λ genome, located in the central region of the λ DNA, between genes J and N, may be replaced by heterologous DNA encoding a desired product. That region is transcribed early during infection.

In order to maximize the expression of a targeted gene, whose synthesis information is recorded in the area of phage's early genes, special conditions for the phage's development should be provided to ensure proper replication. Further, transcription of the early area, containing the targeted gene, should be fostered, while transcription of the later genes, involved in cell lysis, should be decelerated. This slows down maturation of the λ particles and subsequent cell lysis. Consequently, the early phage products, including the targeted gene product, will accumulate in the bacterial cells. Deceleration of late transcription, thereby extending expression of the targeted gene, may be accomplished by: (1) mutations of phage genome that block expression of the later genes (2) increased multiplicity of infection, and/or (3) cultivation of the infected bacterial cells at a reduced temperature.

An advantage of infecting producer cells with a bacteriophage is that the phage causes a profound rearrangement of all macromolecular synthesis in the bacterial host cells. By turning off transcription of bacterial genes, phages may increase the copying of the targeted gene, and consequently, increase the output of desired product.

In one embodiment of the present super-production system, phage λ with amber-mutations that delay bacterial lysis (e.g., Q$^-$ and R$^-$ mutations) are provided in a strain of E. coli, designated Su$^\circ$, which lacks the suppressor responsible for correcting amber-mutations in phage λ. In order to obtain a non-suppressing (Su$^\circ$) strain of E. coli, Su$^\circ$ clones are selected from the wild-type Su$^+$ population. Preferably, a selection marker is inserted into the phage DNA, e.g., tetracycline or ampicillin resistance.

Selection of non-suppressing (Su$^\circ$) strains of E. coli, for example, E. coli K 802 was carried out with phage λ cI$_{857}$ Nam7Nam53 bla tet (hereinafter λ bla N'). Strain E. coli C600 (λ bla N') served as source of the phage. This phage was obtained by insertion of plasmid pCV 11 (bla tet) at EcoRI site into single-site (EcoRI) vector carrying ts-mutation in repressor gene (cI$_{857}$). Then two amber-mutations were introduced into the phage N gene by recombination in vivo.

Clones were tested for non-lysogenicity with phage λ clear. In addition to phage λ bla N', phage λ cI$_{857}$ Q$_{am117}$ R$_{am54}$ was used to check for suppressor.

As is known, phage λ N' mutant is not able to lyse the host cells and is present in cells in the form of extremely unstable plasmids. If the host cells contain suppressor, the amber-mutation is phenotypically corrected, the N protein is synthesized and the phage can develop lytically. This difference in the viability of Su$^+$ and Su$^\circ$ cells, infected by λ N', is used as a basis for selection of spontaneously appearing Su$^\circ$ revertants from the E. coli Su$^+$ cell population. Phage λ with an inserted plasmid that introduced the ampicillin and tetracycline resistance markers into cells was used to prevent the nonlysing Su$^\circ$ cells from masking the search for mutants. The phage also contains ts-mutation in the repressor gene that permits lytic development of such phage resulting in cell lysis.

If the medium supplemented with ampicillin and tetracycline is inoculated with Su$^+$ culture after its infection with phage λ bla N' with subsequent growth at 43° C., single suppressor-free cells containing phage λ bla N' in the form of plasmids should develop on plates. Curing the cells from the phage, we should obtain Su$^\circ$ derivatives of the parent cultures. The method can be subdivided into several stages.

1. Infection of Culture with Phage λ bla N'

The culture E. coli Su$^+$ was grown on the M9 medium with maltose at 37° C. under intense agitation to a density of 1–2×10$^8$ cells/ml. The cells were infected with phage λ bla N' at a multiplicity of 5–10 particles per cell and incubated for 20 min at 20° C. Under given conditions, the infection efficiency is about 100%, in addition to the bulk of Su$^+$ cells, the phage also infects single Su$^\circ$ cells.

2. Selection of Suppressor-Free Cells Containing Marker Phage

After infection, cells were plated out on agar medium supplemented with 12 γ/ml tetracycline and 20 γ/ml ampicillin and grown at 43° C. In 24 h, single colonies developed, which were replated on agar medium with antibiotics and grown at 37° C.

3. Curing of the Selected Clones from Phage λ bla N'

Since phage λ N' in the E. coli Su$^\circ$ cells is in the form of extremely unstable plasmids, in order to cure from the phage the selected clones were plated on selective agar medium without antibiotics and grown at 37° C. The number of cells that had lost the phage in the first passage on the medium without antibiotics amounted to 12–35%. The selection of such cells was carried out by monitoring the loss of antibiotic resistance and the acquisition of sensitivity to phage λ clear.

4. Testing of Cells for Repressor

The ability of phage λ with amber-mutations to form plaques on lawns of cured clones was checked. Isogenic suppressor-free derivatives of the parent E. coli Su$^+$ strains are clones, on which phage λ bla N' did not form plaques, phage λ cI$_{857}$ Q$_{am117}$ R$_{am54}$ produced 1–3×10$^5$ PFU/ml, and phage λ cI$_{857}$ without mutations in genes Q and R produced 1×10$^{10}$ PFU/ml.

Using this method, we obtained Su$^\circ$ revertants of E. coli K 802 Su$^+$. Based on the cell number at the moment of infection and the number of Su$^\circ$ revertants among them, the frequency of occurrence of suppressor-free cells was 3×10$^{-7}$.

In a preferred embodiment, the gene of interest is cloned into pET-24a(+) under the control of the T7 promoter. Any gene of interest may be used in the practice of the claimed invention. Particular examples include but are not limited to human growth hormone, interferon, methionine amino peptidase, human aFGF 134 amino acid form, human aFGF 140 amino acid form, human aFGF 146 amino acid form, and human aFGF 155 form. In an alternate embodiment, the gene of interest may be cloned into both a bacterial plasmid and the λ phage under the control of appropriate promoters. In a most preferred embodiment, chemically synthesized haFGF 155 gene (SEQ ID NO: 1) is cloned into pET-24a(+) under the control of the T7 promoter. The T7 promoter is recognized only by T7 RNA polymerase and is not recognized by the RNA polymerase of E.coli. The obtained plasmid with haFGF 155 gene (phaFGF 155) was transformed into E. coli BL21(DE3). This strain contains the T7 RNA polymerase gene. The T7 RNA polymerase gene is under the control of the inducible lac UV5 promoter in order to induce T7 RNA polymerase synthesis only when necessary as this protein is toxic for the E. coli cell. The induction of the lac promoter is carried out by adding IPTG to the nutrient medium. In order to obtain the haFGF 155 protein, the producer strain, containing the recombinant plasmid with the haFGF 155 gene, is cultured under conditions of intensive aeration to a cell density of $5 \times 10^7$–$5 \times 10^9$ cells in 1 ml at a temperature of 20–40° C. Then it is infected by lambda phage with the ts-mutation cI repressor gene with a multiplicity from 0.1 to 100 phage bodies per cell and incubation is continued at 20–37° C. for 2–14 hours. Simultaneously with the phage, IPTG at a concentration of 1 mM is introduced.

The haFGF155 gene encodes a protein containing 155 amino acid residues. However, it has only been possible to isolate two shorter aFGF forms from tissue samples. The two isolated forms contain 140 and 134 amino acid residues. The aFGF form containing 140 amino acids is considered complete, while the aFGF form containing 134 amino acids is considered to be truncated. It has not been possible to extract the aFGF form containing 155 amino acids from tissue samples. It is not known whether the shorter isoforms occur as a normal function of cell processing or as an artefact produced during the isolation procedure by specific proteases in the process of aFGF extraction. Western Blot analysis of the protein produced from the isolated DNA recombinant molecules for the three aFGF forms showed high expression of the 140 and 134 forms and a low expression level of the 155 form.

In a preferred embodiment of the present invention, the gene for human acidic fibroblast growth factor encodes the 155 amino acid form of the aFGF protein and is chemically synthesized (SEQ ID NO: 1). The nucleotide sequence of the haFGF 155 gene has been deduced on the basis of the previously described haFGF 155 amino acid sequence (SEQ ID NO: 2). The amino acid sequence of the synthesized haFGF 155 gene does not differ from those previously described such as the translated sequence of the FGF nucleotide sequence of SEQ ID NO: 3. However, the preferred nucleotide sequence of haFGF gene differs from those previously described. In a preferred embodiment of the present invention, the haFGF 155 gene has been chemically synthesized using the codons which are most often used by E. coli for intensively synthesized bacterial proteins. Codon usage tables for E. coli are well known and available. Chemical synthesis of human aFGF genes was carried out by well known methods (Edge et al. (1983) Nucleic Acids Research 11(18): 6419–6435).

Alternatively, any gene of interest may be used in the practice of the present invention including, but not limited to, isolated DNA from animal tissues encoding other forms of the haFGF protein known to those skilled in the art including the 146, the 140 and 134 isoforms and any variants, derivatives, analogs or fragments thererof. Also exemplified herein are genes encoding human growth hormone, human interferon and E. coli methionine amino peptidase.

FIG. 1 shows the complete nucleotide sequence of the haFGF 155 gene, as synthesized by the present inventors (SEQ ID NO: 1) and also a sequence for human acidic fibroblast growth factor from GenBank (SEQ ID NO:3). These two sequences are compared in FIG. 2. There are distinctions in 80 codons.

Expression and cloning vectors typically contain a promoter that is recognized by the host organism and is operably linked to the gene of interest. Promoters are untranslated sequences located upstream (5') to the start codon of a structural gene (generally within 100–1000 base pairs) that control the transcription and translation of particular nucleic acid sequences to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by prokaryotic host cells are known. One skilled in the art would know how to ligate them to a gene of interest using suitable linkers or adaptors to provide appropriate restriction sites.

A preferred promoter system is the E. coli bacteriophage T7 promoter system. The E. coli bacteriophage T7 promoter is very specific and requires the presence of the T7 RNA polymerase. The T7 RNA polymerase may be supplied by transformation with a plasmid expressing the gene for T7 RNA polymerase or may be supplied by induction of a T7 polymerase gene contained on a λ lysogen in a host strain. The T7 promoter and T7 RNA polymerase are commercially available.

Transformation means introducing DNA into an organism so that the DNA is capable of replication, either as an extrachromosomal element or by integration into the chromosome. Transformation of prokaryotic cells is performed using techniques well known to those skilled in the art such as treatment with $CaCl_2$ or electroporation.

Super production of the recombinant proteins was achieved by cultivation of the producer strain under conditions which slow down the lytic development of the lambda phage Such conditions include lowered temperature of cultivation and use of amber mutations in late lambda phage genes such as Q and R genes.

The recombinant proteins are accumulated in the culture medium as a soluble protein as a result of the producer strain cells lysis by lambda phage. The output of recombinant protein generally constituted 20% of the soluble proteins accumulated in the culture medium. Debris was removed from the culture medium by centrifugation. The recombinant proteins can then be purified from contaminant soluble proteins and polypeptides with purification procedures, which are well known to those skilled in the art. Such procedures include, but are not limited to, fractionation on an ion-exchange column, ethanol precipitation, reverse phase HPLC, immunoaffinity, SDS-PAGE, ammonium sulfate precipitation, and gel filtration. In the case of haFGF proteins, the haFGF protein was applied to heparin sepharose in order to obtain purified haFGF.

A more detailed description of the present invention is provided below. While the described embodiment represents the preferred embodiment of the present invention, it is to be understood that modifications will occur to those skilled in the art without departing from the spirit of the invention. The scope of the invention is therefore to be determined solely by the appended claims.

EXAMPLE 1
Production of Human aFGF 155 by Phage-Dependent Method

Figure 3:
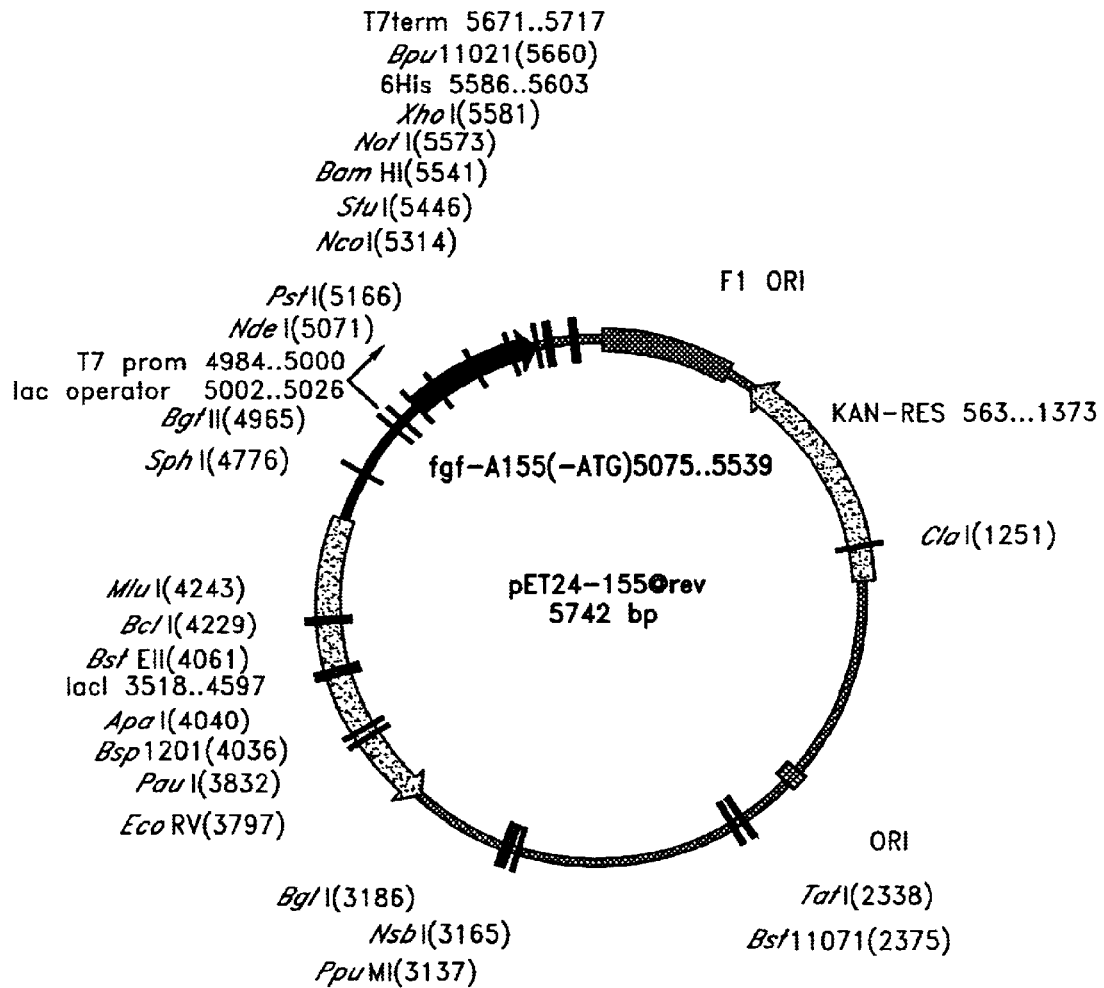
FIG. 3 shows the pET24-155@rev construct which contains the chemically synthesized haFGF 155 gene (SEQ ID NO: 1).

Cultures of *Escherichia coli* BL21(DE3) (NOVAGEN) were transformed by plasmid pET24-155@rev (FIG. 3), which contains one copy of the haFGF 155 gene encoding human acidic fibroblast growth factor (155 amino acids). Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the chemically synthesized haFGF 155 gene (SEQ ID NO: 1) under the control of the T7 promoter to produce plasmid pET24-155@rev. Expression of the haFGF 155 gene begins only after the appearance of T7 polymerase in the cells which is mediated through the induction of the lac UV5 promoter by IPTG.

Cultures of *E. coli* BL21(DE3) with pET24-155@rev were grown with shaking at 37° C. in LB medium, containing 50 µg/ml kanamycin, to a density of 2×10⁸ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Q_{am117}$ $R_{am54}$ was prepared from lysogenic cultures of *E. coli* RLMI, which were grown in LB medium at 30° C. with intensive aeration to a density of approximately 1×10⁸ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10¹⁰ PFU/ml.

After incubation with the phage-infected cells for 14 hours, debris was removed from the culture medium by centrifugation. The culture medium, containing the haFGF 155 protein was applied to a heparin sepharose column to obtain pure haFGF 155.

Figure 4:
FIG. 4 shows HPLC purified haFGF 155. In the electrophoregram: lane 1, 10 μl of the conditioned medium containing recombinant haFGF 155; lane 2, 7 μl of Heparin-Sepharose purified recombinant haFGF 155 (0.45 μg/μl); lane 3, 14 μl out of 80 μl of HPLC-purified haFGF 155. The unmarked lane at the far left contains molecular weight standards.

The culture medium containing the haFGF 155 was analyzed by SDS-polyacrylamide gel electrophoresis under denaturing conditions and stained with Coomassie Blue. An electrophoregram of the culture medium, containing haFGF 155 protein is compared to purified haFGF protein in FIG. 4. Lane 1 shows 10 µl of the culture medium. Lane 2 shows 7 µl of Heparin-Sepharose purified haFGF 155 protein (0.45 µg/µl). Lane 3 shows 14 µl out of 80 µl of HPLC purified ha FGF-155. The unmarked lane at the far left contains molecular weight standards (Amersham Pharmacia Biotech). The production of haFGF 155 protein in phage-infected cultures was about 20% of the total cellular protein. The molecular weight of haFGF 155 was 17, 908 Daltons as determined by densitometer Image Master VDS (data not shown).

Human aFGF 155 produced by the method disclosed above had biological activity based upon the chick membrane assay (Example 6). In addition, purified human aFGF155 showed bioactivity in a cell-based proliferation assay utilizing BALB/c 3T3 fibroblasts (Linemeyer, U.S. Pat. No. 5,401,832). The half-maximal stimulation of cell proliferation occurred at a concentration of 32 pg/ml aFGF155. Unpurified human aFGF155, contained in the bacterial culture medium, also displayed biological activity in the 3T3 fibroblast assay which was equivalent to purified aFGF155, indicating that aFGF155 was synthesized initially in bacteria as a soluble, biologically-active protein.

Figure 5:
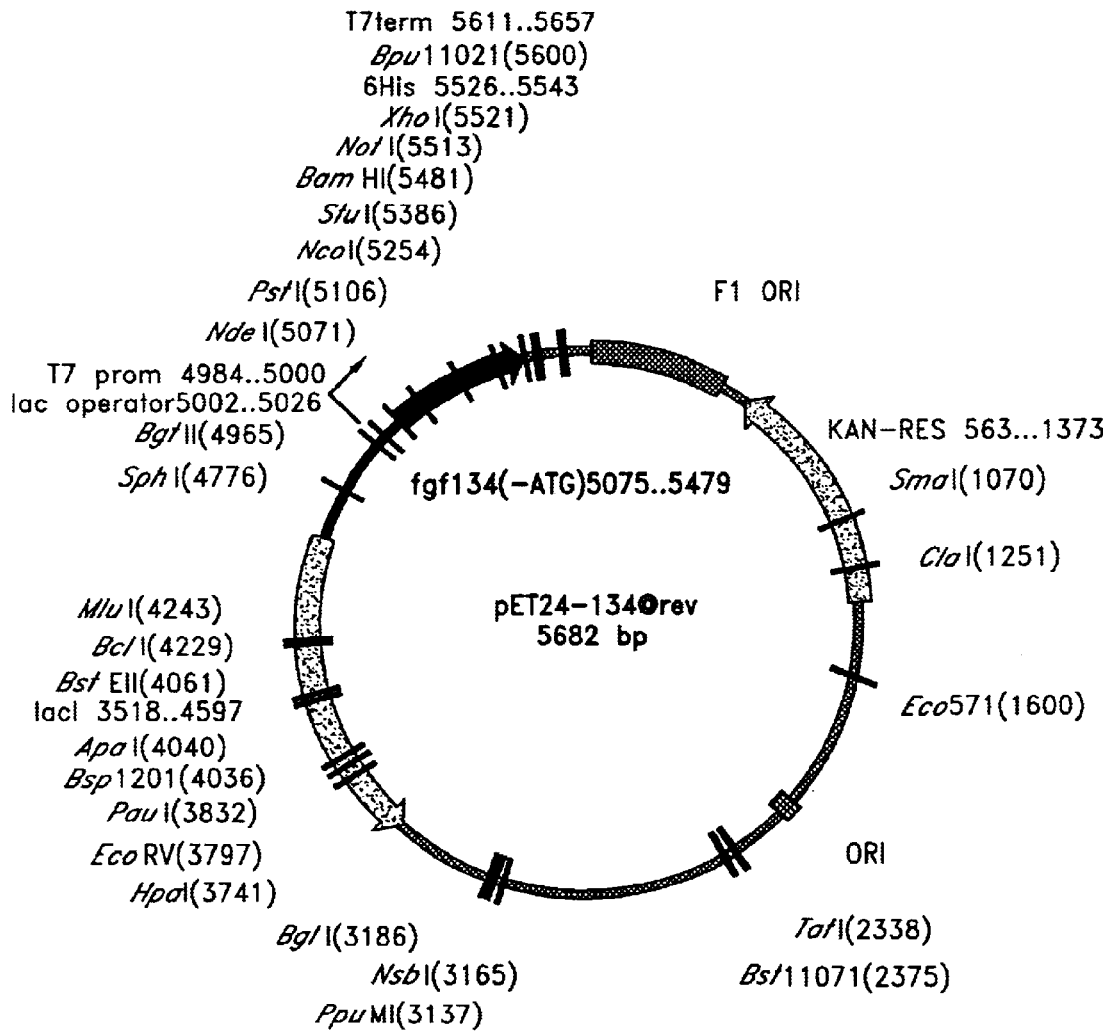
FIG. 5 shows the pET24-134@rev construct which contains the chemically synthesized haFGF 134 gene (SEQ ID NO: 4).

EXAMPLE 2
Production of Human aFGF 134 Amino Acid Form by Phage-Dependent Method Cultures of *Escherichia coli* BL21(DE3) (NOVAGEN) were transformed by plasmid pET24-134@rev (FIG. 5), which contains one copy of the chemically synthesized gene encoding human aFGF (134 amino acids) (FIG. 6; SEQ ID NO: 4). The translated amino acid sequence is shown in SEQ ID NO: 5. Cultures of BL21 (DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 134 amino acid form gene under the control of the T7 promoter. Expression of the human aFGF 134 amino acid form gene begins only after the appearance of T7 polymerase in the cells which is mediated through the induction of the lac UV5 promoter by IPTG.

Cultures of *E. coli* BL21(DE3) with plasmid pET24-134@rev were grown with shaking at 37° C. in LB medium, containing 50 µg/ml kanamycin, to a density of 2×10⁸ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Q_{am117}$ $R_{am54}$ was prepared from lysogenic cultures of *E. coli* RLMI, which were grown in LB medium at 30° C. with intensive aeration to a density of approximately 1×10⁸ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10¹⁰ PFU/ml.

After incubation with the phage-infected cells for 14 hours, debris was removed from the culture medium by centrifugation. The culture medium, containing the haFGF 134 protein was applied to a heparin sepharose column to obtain pure human aFGF 134 protein.

Figure 7:
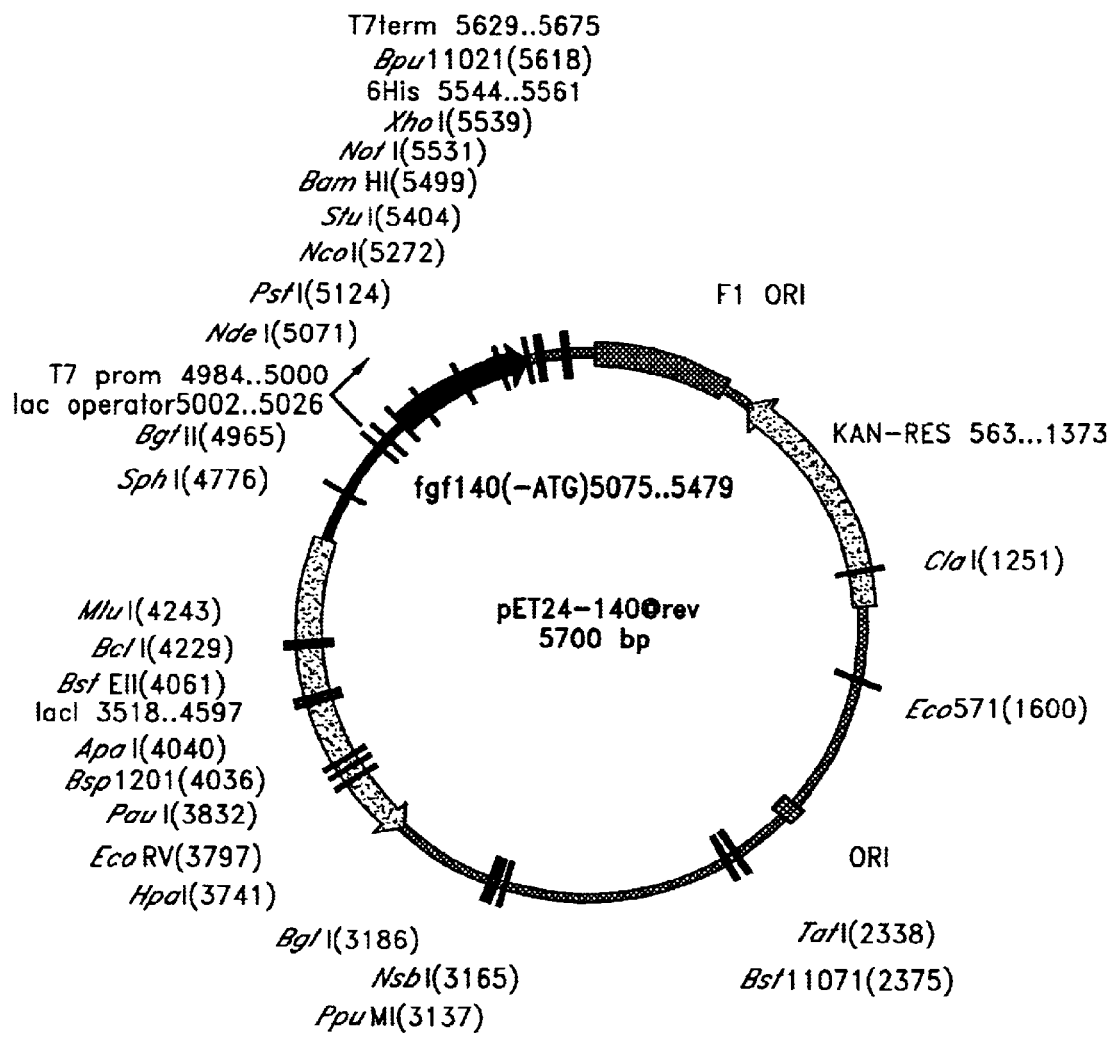
FIG. 7 shows the pET24-140 @rev construct which contains the chemically synthesized haFGF 140 gene (SEQ ID NO: 6).

EXAMPLE 3
Production of Human aFGF 140 Amino Acid Form by Phage-Dependent Method Cultures of *Escherichia coli* BL21(DE3) (NOVAGEN) were transformed by plasmid pET24-140@rev (FIG. 7), which contains one copy of the chemically synthesized gene encoding human aFGF (FIG. 8; 140 amino acids) (SEQ ID NO: 6). The corresponding protein is shown as SEQ ID NO: 7. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 140 amino acid form gene under the control of the T7 promoter. Expression of the human aFGF 140 amino acid form gene begins only after the appearance of T7 polymerase in the cells which is mediated through the induction of the lac UV5 promoter by IPTG.

Cultures of *E. coli* BL21(DE3) with pET24-140@rev were grown with shaking at 37° C. in LB medium, containing 50 μg/ml kanamycin, to a density of 2×10$^8$ cells/ml. Then the cells were infected with phage λ cI$_{857}$ Q$_{am117}$ R$_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ cI$_{857}$ Q$_{am117}$ R$_{am54}$ was prepared from lysogenic cultures of *E. coli* RLMI, which were grown in LB medium at 30° C. with intensive aeration to a density of approximately 1×10$^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10$^{10}$ PFU/ml.

After incubation with the phage-infected cells for 14 hours, debris was removed from the culture medium by centrifugation. The culture medium, containing the haFGF 140 amino acid form was applied to a heparin sepharose column to obtain pure human aFGF 140.

Human aFGF 140 produced by the method disclosed above had biological activity based upon the chick membrane assay (Example 6).

EXAMPLE 4
Production of Human aFGF 146 Amino Acid Form by Phage-Dependent Method Cultures of *Escherichia coli* BL21(DE3) (NOVAGEN) were transformed by plasmid pET24-146@rev, which contains one copy of the chemically synthesized gene encoding human aFGF (146 amino acids) (not shown). Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human aFGF 146 amino acid form gene under the control of the T7 promoter. Expression of the human aFGF 146 amino acid form gene begins only after the appearance of T7 polymerase in the cells which is mediated through the induction of the lac UV5 promoter by IPTG.

Cultures of *E. coli* BL21(DE3) with pET24-146@rev were grown with shaking at 37° C. in LB medium, containing 50 pg/ml kanamycin, to a density of 2×10$^8$ cells/ml. Then the cells were infected with phage λ cI$_{857}$ Q$_{am117}$ R$_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ cI$_{857}$ Q$_{am117}$ R$_{am54}$ was prepared from lysogenic cultures of *E. coli* RLMI, which were grown in LB medium at 30° C. with intensive aeration to a density of approximately 1×10$^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at 1–2×10$^{10}$ PFU/ml.

After incubation with the phage-infected cells for 14 hours, debris was removed from the culture medium by centrifugation. The culture medium, containing the haFGF 146 protein was applied to a heparin sepharose column to obtain pure human aFGF 146.

Human aFGF 146 produced by the method disclosed above had biological activity based upon the chick membrane assay (Example 6).

EXAMPLE 5
Purification of Recombinant haFGF Proteins

The culture medium containing a haFGF protein is diluted with one volume of 0.04M KH$_2$PO$_4$ buffer, pH 7.0, and applied to a heparin-sepharose column equilibrated with 0.02 M KH$_2$PO$_4$, pH 7.0. The flow rate is adjusted to 80 ml/hour. After application of the culture medium containing the haFGF protein, the column is washed with 0.02M KH$_2$PO$_4$ buffer, pH 7.0. Next, the column is washed with 0.02 M KH$_2$PO$_4$ buffer containing 0.6M NaCl, pH 7.3. Elution is carried out using 0.02 M KH$_2$PO$_4$ buffer with 1.5 M NaCl, pH 7.5. All steps are carried out at 4° C.

EXAMPLE 6
A Method of Studying FGF Influence on the Formation of New Blood Vessels in the Chicken Embryo Chorio-Allantoic Membrane (CAM).

The method of studying angiogenesis on the model of chicken embryos (Thomas et al. (1985) Proc. Natl. Acad. Sci, USA 82: 6409–6413) was adapted to determine the effects of the haFGF 155, 146, and 140 recombinant proteins on angiogenesis compared to pure brain-derived acidic fibroblast growth factor. Pure brain-derived acidic fibroblast growth factor is a potent angiogenic vascular endothelial cell mitogen with sequence homology to interleukin.

The shells of three-day old chicken embryos were sterilized with ethyl alcohol. The shell and under shell cover were removed from the air chamber using forceps and the eggs were covered by the bottom of a plastic 35 mm Petri dish. The embryos were incubated at 37° C. for 5–6 days. At the end of this period, the embryos were examined and the eggs with well-developed blood vessels of CAM were selected for experimentation.

Filter paper disks with deposited gel containing FGF were laid on the eggs CAM with the gel towards the blood vessels and incubated in a thermostat at 37° C. for another 3 days. The gel was prepared in the following way: the tested quantity of FGF was dissolved in 30 μl of Eagle's medium (solution 1); then in 30 μl of Eagle's medium, 10 μg of heparin was dissolved and 2% of agarose added (solution 2). Then equal volumes of solution 1 and 2 were mixed and the obtained mixture was deposited in aliquots by 60 μl on 12 mm diameter filter paper disks.

On the 4$^{th}$ day, the filter paper disks were removed. Rich cow milk (10% milkfat) was injected under CAM in a quantity of about 1 ml or less. The result was a white background against which the CAM vessels were easily observed.

The results of the experiment were recorded with a video camera in conjunction with a computer. The formation of new CAM vessel under the affect of FGF was evaluated by the following parameters: the nature and direction of vessel growth, their quantity and quality (large, medium, small), the presence or absence of anastomosis, etc. These data were compared with the control samples which had not been exposed to FGF. Chicken embryo blood vessels on the 14$^{th}$ day of development were treated with FGF155 produced by the phage-dependent recombinant method described herein and purified on heparin sepharose as described.

Application of recombinant FGF155 protein demonstrated the formation of new blood vessels. On the fourth day after application of 1 μg of FGF155, vessels were mainly small and showed radial growth. Increasing the amount of FGF155 to 3 μg showed a corresponding increase in the size of the blood vessels. Medium vessels were observed with radial growth. A further increase to 4 μg of FGF155 applied showed development of large, medium and small blood vessels at 4 days after application as compared to control.

EXAMPLE 7
Production of Human Growth Hormone by Phage-Dependent Method

Cultures of *Escherichia coli* BL21(DE3) (NOVAGEN) were transformed by a plasmid which contains one copy of a chemically synthesized gene encoding human growth hormone (SEQ ID NO: 8). The translated amino acid sequence is shown as SEQ ID NO: 9. Cultures of BL21 (DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the human growth hormone gene under the control of the T7 promoter. Expression of the human growth hormone gene begins only after the appearance of T7 polymerase in the cells which is mediated through the induction of the lac UV5 promoter by IPTG.

The transformed cultures of *E. coli* BL21(DE3) were grown with shaking at 37° C. in LB medium, containing 50 μg/ml kanamycin, to a density of $2 \times 10^8$ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Q_{am117}$ $R_{am54}$ was prepared from lysogenic cultures of *E. coli* RLMI, which were grown in LB medium at 30° C. with intensive aeration to a density of approximately $1 \times 10^8$ cells/ml. The lysogenic culture was warmed to 43° C. and incubated for 20 minutes to inactivate cI repressor. The temperature was then decreased to 37° C. and after 60–70 minutes the bacterial cells underwent lysis, with phages being formed at $1-2 \times 10^{10}$ PFU/ml.

After incubation with the phage-infected cells for 14 hours, debris was removed from the culture medium by centrifugation. The human growth hormone protein was purified by column chromatography by methods known to those skilled in the art to obtain pure human growth hormone. The purified human growth hormone was biologically active when assayed in a cell-based bioassay utilizing Nb2 lymphoma cells (Gout P W, *Cancer Research* 40:2433–2436, 1980). The concentration of human growth hormone that gave half-maximal stimulation of Nb2 cell proliferation was 125 pg/ml.

EXAMPLE 8
Production of Human Interferon α-2b by Phage-Dependent Method

Figure 9:
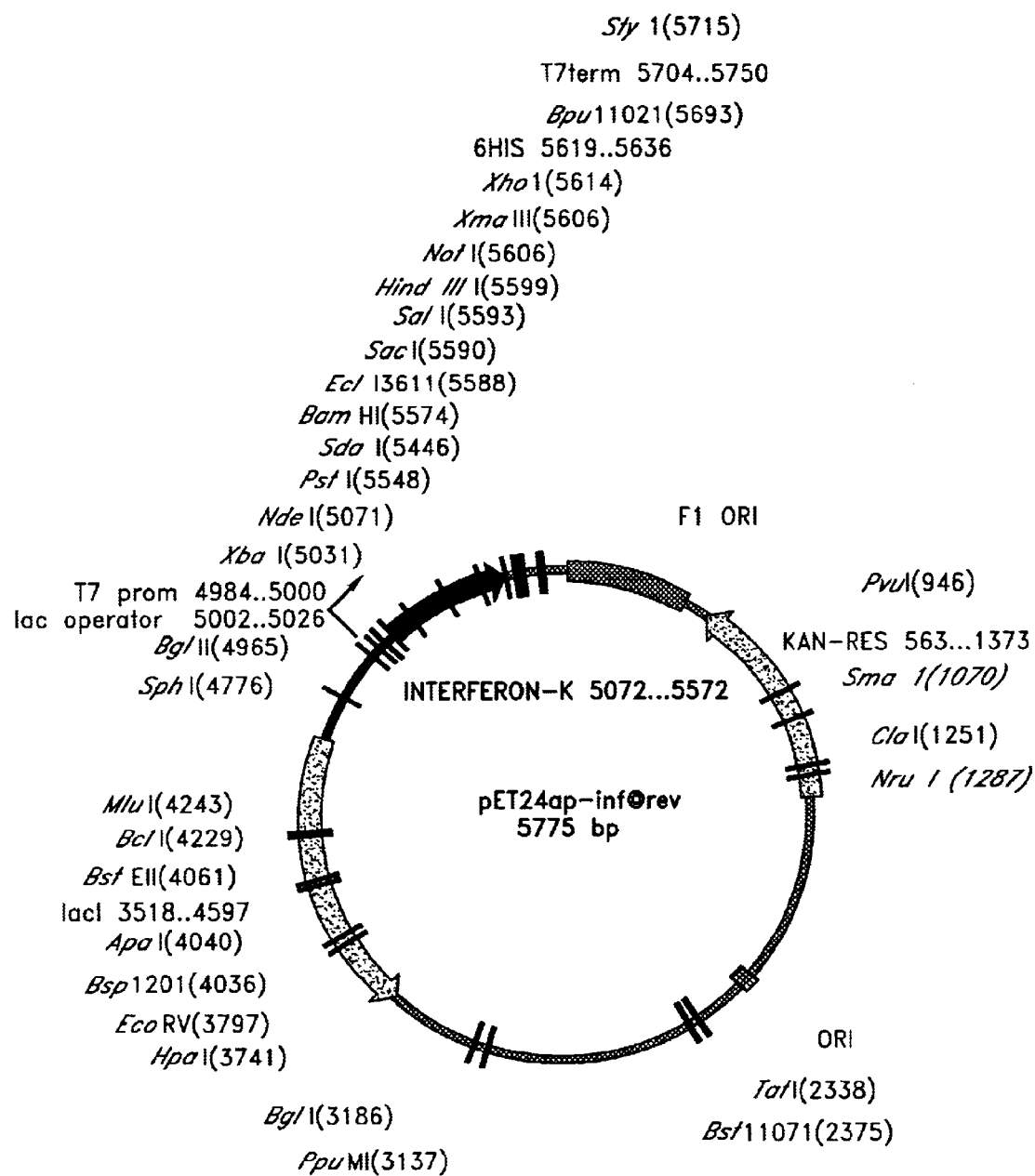
FIG. 9 shows the pET24ap-inf@rev construct which contains the chemically synthesized interferon α-2b gene (SEQ ID NO: 10).

Cultures of *Escherichia coli* BL21(DE3) (NOVAGEN) were transformed by plasmid pET24ap-inf@rev (FIG. 9), which contains one copy of a chemically synthesized gene encoding α-2 human interferon (FIG. 10; SEQ ID NO: 10). The translated amino acid sequence is shown as SEQ ID NO: 11. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the interferon gene under the control of the T7 promoter. Expression of the interferon gene begins only after the appearance of T7 polymerase in the cells which is mediated through the induction of the lac UV5 promoter by IPTG.

Cultures of *E. coli* BL21(DE3) with plasmid pET24ap-inf@rev were grown with shaking at 37° C. in LB medium, containing 50 μg/ml kanamycin, to a density of $2 \times 10^8$ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Q_{am117}$ $R_{am54}$ was prepared from lysogenic cultures of *E. coli* RLMI, which were grown in LB medium at 30° C. with intensive aeration to a density of approximately $1 \times 10^8$ cells/ml. The lysogenic culture was warmed to 43° C. and incubated for 20 minutes to inactivate CI repressor. The temperature was then decreased to 37° C. and after 60–70 minutes the bacterial cells underwent lysis, with phages being formed at $1-2 \times 10^{10}$ PFU/ml.

After incubation with the phage-infected cells for 14 hours, debris was removed from the culture medium by centrifugation. Interferon was purified by column chromatography by methods known to those skilled in the art to obtain pure interferon.

Interferon produced by the disclosed method had biological activity based upon the interferon antiviral assay performed in vesicular stomatitus virus infected bovine kidney cells (Aebersold P, *Methods in Enzymology* 119:579–592, 1986). Interferon alpha 2b had a biological potency of $1.81 \times 10^8$ International Units (IU) per mg protein in this assay. Interferon alpha 2b contained in the bacterial culture media prior to purification had an equivalent potency to the purified interferon in this antiviral assay, indication that interferon alpha 2b is initially synthesized in bacteria as a soluble, biologically-active protein.

EXAMPLE 9
Production of *E. coli* Methionine Amino Peptidase by Phage-Dependent Method Cultures of *Escherichia coli* BL21(DE3) (NOVAGEN) were transformed by a plasmid which contains one copy of a chemically synthesized gene encoding *E. coli* methionine amino peptidase. Cultures of BL21(DE3) contain a single copy of the gene for T7 RNA polymerase under the control of the inducible lac UV5 promoter in the bacterial genome (Studier et al. (1986) J. Mol. Biol. 189: 113–130). Into the plasmid pET-24a(+) (NOVAGEN) was inserted the *E. coli* methionine amino peptidase gene under the control of the T7 promoter. Expression of the *E. coli* methionine amino peptidase gene begins only after the appearance of T7 polymerase in the cells which is mediated through the induction of the lac UV5 promoter by IPTG.

The transformed cultures of *E. coli* BL21(DE3) were grown with shaking at 37° C. in LB medium, containing 50 μg/ml kanamycin, to a density of $2 \times 10^8$ cells/ml. Then the cells were infected with phage λ $cI_{857}$ $Q_{am117}$ $R_{am54}$ at a multiplicity of about 10 phage bodies per 1 bacterial cell and cultivated with shaking at 21° C. for about 14 hour. Simultaneously with phage, 1 mM IPTG was introduced into the medium.

Phage λ $cI_{857}$ $Q_{am117}$ $R_{am54}$ was prepared from lysogenic cultures of *E. coli* RLMI, which were grown in LB medium at 30° C. with intensive aeration to a density of approximately $1 \times 10^8$ cells/ml. The lysogenic culture was warmed to 43° C. and incubated for 20 minutes to inactivate CI repressor. The temperature was then decreased to 37° C. and after 60–70 minutes the bacterial cells underwent lysis, with phages being formed at $1-2 \times 10^{10}$ PFU/ml.

After incubation with the phage-infected cells for 14 hours, debris was removed from the culture medium by centrifugation. *E. coli* methionine amino peptidase was purified by column chromatography by methods known to those skilled in the art to obtain pure *E. coli* methionine amino peptidase.

EXAMPLE 10
Gel Analysis of Recombinant Proteins Produced by the Phage-Dependent Method.

Figure 11:
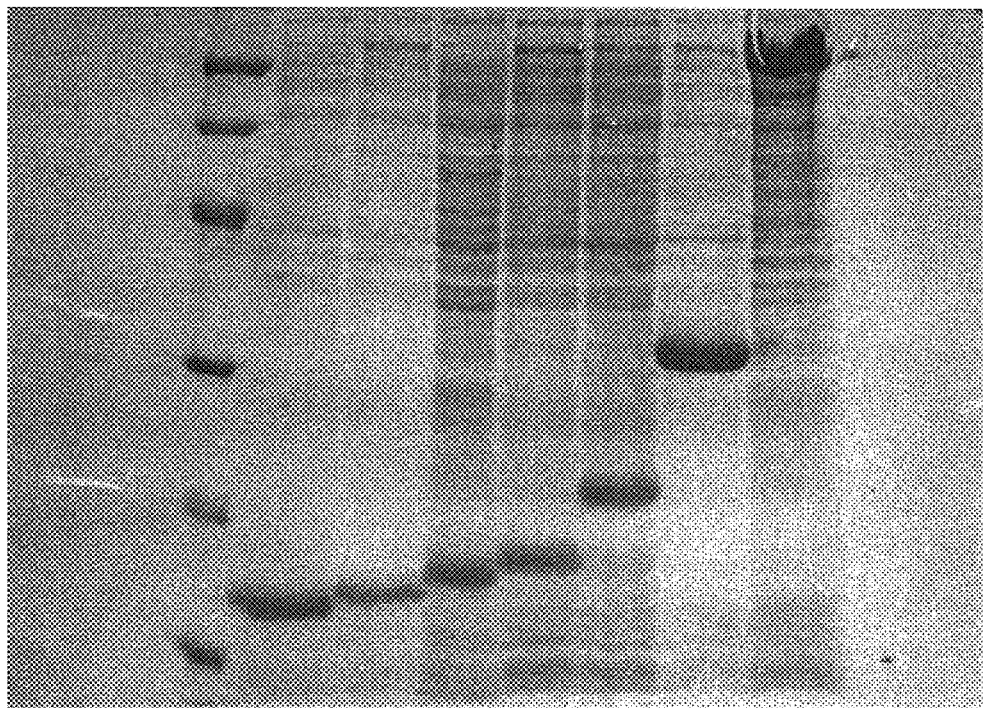
FIG. 11 shows a 12.5% SDS polyacrylamide gel containing proteins produced by the phage-dependent method described herein: lane 1, molecular weight standards, 2 μg each standard; lane 2, 40 μl of culture media containing the recombinant FGF 134 protein; lane 3, 40 μl of culture media containing the recombinant FGF 140 protein; lane 4, 40 μl of culture media containing recombinant interferon α2B.

Culture media containing human aFGF 134 amino acid form, human aFGF 140 amino acid form, human aFGF 155 amino acid form, human growth hormone, interferon, and methionine aminopeptidase were analyzed by SDS-polyacrylamide gel electrophoresis under denaturing conditions and stained with Coomassie Blue. An electrophoregram of culture media, containing human aFGF 134 amino acid form, human aFGF 140 amino acid form, human aFGF 146 amino acid form, human growth hormone, and interferon proteins is compared to molecular weight standards in FIG. 11. Lane 2 shows 30 µl of the culture medium containing human aFGF 134 amino acid form. Lane 3 shows 30 µl of culture media containing the recombinant FGF 140 protein. Lane 4 shows 30 µl of culture media containing recombinant interferon. Lane 5 shows 30 µl of culture media containing recombinant FGF 155 protein. Lane 6 shows 30 µl of culture media containing recombinant human growth hormone. Lane 7 shows 30 µl of culture media containing recombinant methionine aminopeptidase. Lane 1 shows 2 µg of each molecular weight standard (Amersham Pharmacia Biotech). From the top, the molecular weight standards are: 94,000; 67,000; 43,000; 30,000; 20,100; and 14,400.

Quantitation of amounts of human aFGF 134 amino acid form, human aFGF 140 amino acid form, human aFGF 155 amino acid form, human growth hormone, interferon, and methionine aminopeptidase in a mixture was accomplished by scanning the stained protein bands on a polyacrylamide gel with densitometer Image Master VDS (Pharmacia Biotech). The production of the recombinant proteins in phage-infected cultures was about 20% of the total cellular protein.

An electrophoregram containing purified purified recombinant human aFGF 134, haFGF 140, ha FGF 146, interferon, haFGF 155 and methionine aminopeptidase protein was compared to molecular weight standards (FIG. 12). Lane 2 shows 5 µg of the purified aFGF 134 protein. Lane 3 shows 5 µg of the purified human aFGF 140. Lane 4 shows 5 µg of the purified human aFGF 146 amino acid form. The production of human aFGF 146 amino acid form in phage-infected cultures was about 20% of the total cellular protein. Lane 5 shows 5 µg of purified interferon. Lane 6 shows 5 µg of haFGF 155 protein. Lane 7 shows 5 µg of the purified *E. coli* methionine amino peptidase. Lanes 1 and 8 show 2 µg of each molecular weight standard (Amersham Pharmacia Biotech).

It will be understood by those of skill in the art that numerous and various modifications can be made without departing from the spirit of the present invention. Therefore, it should be clearly understood that the forms of the present invention are illustrative only and are not intended to limit the scope of the present invention.

---

What is claimed is:

1. A method for producing a biologically active protein, comprising:
    transforming a strain of E. coli with a plasmid having at least one copy of an expressible gene encoding a biologically active protein, operably linked to a polymerase promoter, wherein the E. coli strain comprises a gene for T7 RNA polymerase;
    infecting the transformed bacterial host cell with a bacteriophage λ capable of mediating delayed lysis; and
    cultivating the E. coli host cell under a culture condition that induces growth of said cell without lysis, and producing said protein as a soluble, biologically-active protein.

2. The method of claim 1, wherein the bacteriophage λ has a temperature-sensitive mutation.

3. The method of claim 2, wherein the temperature-sensitive mutation is $cI_{857}$.

4. The method of claim 2, wherein prior to the cultivating step, the E. coli host cells are grown at a temperature which prevents lytic growth of the bacteriophage λ.

5. The method of claim 1, wherein the bacteriophage λ has a mutation in at least one gene capable of mediating delayed lysis.

6. The method of claim 5, wherein the at least one gene capable of mediating delayed lysis is selected from the group consisting of N, Q and R.

7. The method of claim 1, wherein the strain of E. coli produces a suppressor for the repair of amber-mutations.

8. The method of claim 1, wherein the strain of E. coli lacks a suppressor for the repair of amber-mutations.

9. The method of claim 1, wherein the infecting bacteriophage λ is provided at a multiplicity of infection in a range of about 1 to about 100.

10. The method of claim 1 wherein the infecting bacteriophage λ is provided at a multiplicity of infection in a range of about 10 to about 25.

11. The method of claim 1, wherein bacteriophage-mediated delayed lysis of the strain of E. coli is delayed at higher multiplicities of infection relative to lower multiplicities of infection.

12. The method of claim 1, wherein the expressible gene encodes a human acidic fibroblast growth factor.

13. The method of claim 12, wherein the human acidic fibroblast growth factor contains 134 amino acids.

14. The method of claim 12, wherein the human acidic fibroblast growth factor contains 140 amino acids.

15. The method of claim 12, wherein the human acidic fibroblast growth factor contains 146 amino acids.

16. The method of claim 12, wherein the human acidic fibroblast growth factor contains 155 amino acids.

17. The method of claim 16, wherein the human acidic fibroblast growth factor has the sequence as set forth in SEQ ID NO: 1.

18. The method of claim 1, wherein the expressible gene encodes a human growth hormone.

19. The method of claim 1, wherein the expressible gene encodes a human interferon.

20. The method of claim 1, wherein the expressible gene encodes an E. coli methionine amino peptidase.

21. The method of claim 1, wherein the gene for T7 RNA polymerase is under the control of an inducible promoter.

22. The method of claim 21, wherein the inducible promoter is a lac UV 5 promoter.

23. A method of producing a biologically active protein comprising:
    a) growing a first strain of E. coli cells, which harbor a strain of bacteriophage λ, wherein the bacteriophage λ has a temperature-sensitive mutation,
    b) adjusting the temperature to provide for lysis of the first strain of E. coli cells and release of the bacteriophage λ,
    C) providing a second strain of E. coli cells which have been transformed with a plasmid having at least one copy of an expressible gene encoding said biologically active protein, said expressible gene being operably linked to a T7 polymerase promoter, wherein the second strain of E. coli cells comprises a gene for T7 RNA polymerase that may be induced by addition of an inducer;
    d) infecting the second strain of E. coli cells with the bacteriophage λ released from the first strain of E. coli cells; and
    e) cultivating the infected second strain of E. coli cells under a culture condition that delayed lysis of the infected E. coli cells and in a culture medium containing the inducer, such that protein is produced and released into the culture medium upon lysis of the second strain of E. coli cells, wherein said protein is produced as a soluble, biologically-active protein.

* * * * *